(12) United States Patent
Jesudason et al.

(10) Patent No.: US 7,846,950 B2
(45) Date of Patent: Dec. 7, 2010

(54) HISTAMINE H3 RECEPTOR INHIBITORS, PREPARATION AND THERAPEUTIC USES

(75) Inventors: Cynthia Darshini Jesudason, Indianapolis, IN (US); Freddie Craig Stevens, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 685 days.

(21) Appl. No.: 11/577,388

(22) PCT Filed: Oct. 11, 2005

(86) PCT No.: PCT/US2005/036023

§ 371 (c)(1),
(2), (4) Date: Apr. 17, 2007

(87) PCT Pub. No.: WO2006/044228

PCT Pub. Date: Apr. 27, 2006

(65) Prior Publication Data

US 2008/0015235 A1    Jan. 17, 2008

Related U.S. Application Data

(60) Provisional application No. 60/619,785, filed on Oct. 18, 2004.

(51) Int. Cl.
*A61K 31/422*   (2006.01)
*A61K 31/4025*  (2006.01)
*A61K 31/4245*  (2006.01)
*C07D 417/12*   (2006.01)
*C07D 405/12*   (2006.01)
*A61P 25/00*    (2006.01)

(52) U.S. Cl. ................ 514/364; 514/365; 514/378; 514/422; 548/131; 548/204; 548/247; 548/518; 548/527

(58) Field of Classification Search ............. None
See application file for complete search history.

(56) References Cited

U.S. PATENT DOCUMENTS

2009/0118254 A1 *   5/2009   Beavers et al. ......... 514/210.18

FOREIGN PATENT DOCUMENTS

| WO | WO 02/076925 | 10/2002 |
|----|--------------|---------|
| WO | WO 2005/121080 | 12/2005 |

* cited by examiner

*Primary Examiner*—Kamal A Saeed
(74) *Attorney, Agent, or Firm*—Dan L. Wood

(57) ABSTRACT

The present invention provides novel compounds with histamine-H3 receptor antagonist or inverse agonist activity. In particular, the invention provides a compound of Formula I, or a pharmaceutically acceptable salt thereof, pharmaceutical compositions comprising the compounds, methods of treatment employing these compounds and compositions, and intermediates and methods for making these compounds. The invention provides methods of using compounds and pharmaceutical compositions to treat obesity, cognitive deficiencies, narcolepsy, and other histamine H3 receptor-related diseases.

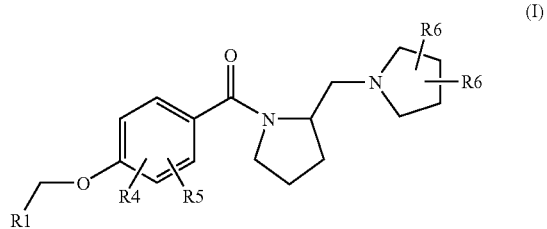

12 Claims, No Drawings

HISTAMINE H3 RECEPTOR INHIBITORS, PREPARATION AND THERAPEUTIC USES

This is the national phase application, under 35 USC 371, for PCT/US2005/036023, filed Oct. 11, 2005, which claims the benefit, under 35 USC 119(e), of U.S. provisional application 60/619,785 filed Oct. 18, 2004.

The present invention relates to novel heteroaromatic aryl compounds, and to the use of these compounds as pharmaceutical compositions, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, H3R inverse agonists or antagonists induce a prolonged wakefulness, improved cognitive function, reduction in food intake, and normalization of vestibular reflexes. Accordingly, the histamine H3 receptor is an important target for new therapeutics in Alzheimer's disease, mood and attention adjustments, cognitive deficiencies, obesity, dizziness, schizophrenia, epilepsy, sleeping disorders, narcolepsy, and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)]. Alternative names for this receptor are PORT3 or H4R. Although relatively selective ligands have been developed for H1R, H2R and H3R, few specific ligands have been developed that can distinguish H3R from H4R. H4R is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently, other imidazole and non-imidazole ligands of the histamine H3 receptor have been described. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of heteroaromatic aryl compounds have a high affinity, selective, and potent activity at the histamine H3 receptor. The subject invention is distinct in the particular structures and their activities.

SUMMARY OF THE INVENTION

The present invention is a compound structurally represented by Formula I:

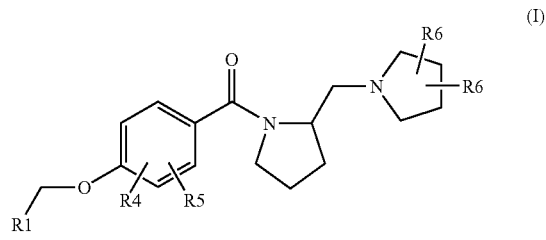

or a pharmaceutically acceptable salt thereof wherein:

R1 is independently
- -HET, wherein each carbon atom of the HET ring is optionally substituted once by R2, and each nitrogen atom of the HET ring is optionally substituted once with R3, provided that the said nitrogen atom is not connected by a double bond to an adjacent ring atom;

R2 is independently at each occurrence
- —H, -halogen, —($C_1$-$C_7$) alkyl (optionally substituted with one to three halogens), —CN, —C(O)R7, —C(O)OR7, —CO(O)Li, —C(O)($C_3$-$C_5$)cycloalkyl, —C(O)NR7R8, —OCF$_3$, —OR7, —NO$_2$, —NR7R8, —NR9SO$_2$R7, —NR9C(O)R7, —NR9CO$_2$R7, —NR9C(O)NR7R8, —SR7, —SO$_2$R7, —SO$_2$CF$_3$, —SO$_2$NR7R8, —S(O)R7, -phenyl-R9, —C(H)═NO—R7, -pyridinyl, -HET-R9, or —($C_1$-$C_7$)alkyl-NHC(O)R7 (provided that not more than one occurrence of R2 is -HET-R9, -phenyl-R9, or -pyridinyl);

R3 is independently at each occurrence
- —H, —($C_1$-$C_7$) alkyl (optionally substituted with one to three halogens), -phenyl, -benzyl, —SO$_2$R7, —C(O)R7, —C(O)NR7R8, or —C(O)OR7;

R4 and R5 are independently
- —H, —OH, -halogen, —($C_1$-$C_3$) alkyl (optionally substituted with one to three halogens), or —OR9;

R6 is independently at each occurrence
- —H, -halogen, —($C_1$-$C_3$) alkyl (optionally substituted with one to three halogens), —NH$_2$, —NR7R8, —OH, or —OR7;

R7 and R8 are independently at each occurrence
—H, or —(C$_1$-C$_7$) alkyl (optionally substituted with one to three halogens), wherein R7 and R8 can combine with the atom to which they are attached to form a three to seven membered ring; and R9 is independently at each occurrence
—H, or —(C$_1$-C$_3$) alkyl (optionally substituted with one to three halogens).

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine. The term "H1R" means the histamine H1 receptor subtype. The term "H2R" means the histamine H2 receptor subtype.

The term "H3R antagonists" is defined as a compound with the ability to block forskolin-stimulated cAMP production in response to agonist R-(−)α methylhistamine. The term "H3R inverse agonist" is defined as a compound with the ability to inhibit the constitutive activity of H3R. "Selective H3R antagonists or inverse agonists" means a compound of the present invention having a greater affinity for H3 histamine receptor than for GPRv53 histamine receptor.

In the formulae of the present document, the general chemical terms have their usual meanings unless otherwise indicated. For example;

"(C$_1$-C$_3$) alkyl" are one to three carbon atoms such as methyl, ethyl, propyl, and the like, optionally substituted with one to three halogens, and "(C$_1$-C$_4$) alkyl" are one to four carbon atoms such as methyl, ethyl, propyl, butyl and the like, optionally substituted with one to three halogens, and "(C$_1$-C$_7$) alkyl" are one to seven carbon atoms such as methyl, ethyl, propyl, butyl, pentyl, hexyl, heptyl, and the like, optionally substituted with one to three halogens. As defined herein "alkyl" includes branched or isomeric forms.

"(C$_3$-C$_5$) Cycloalkyl" means a ring with three to five carbon atoms such as cyclopropyl, cyclobutyl, and cyclopentyl.

The term "HET" represents a stable aromatic heterocyclic ring, containing five atoms, of which one to four are heteroatoms that are the same, or different, and are selected from N, O, and S. The heterocyclic ring of "HET" may be attached to the R1 position of Formula I at any point on the ring which affords a stable structure. Representative "HET" rings include pyrrolyl, isoxazolyl, isothiazolyl, pyrazolyl, oxazolyl, oxadiazolyl, thiadiazolyl, thiazolyl, imidazolyl, triazolyl, tetrazolyl, furanyl, thienyl, thiophenyl, and the like. Further specific examples of five membered heterocycles are described below, and further described in the Preparations and Examples provided herein.

"Halogen" or "halo" means fluoro, chloro, bromo, and iodo.

The term "optionally substituted" as used herein means that the groups in question are either unsubstituted or substituted with one or more of the substituents specified. When the groups in question are substituted with more than one substituent, the substituents may be the same or different. Furthermore, when using the terms "independently", "independently are", and "independently selected from" it should be understood that the groups in question may be the same or different. Certain of the defined terms herein may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating", and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s), Formula I, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The term "suitable solvent" refers to any solvent, or mixture of solvents, inert to the ongoing reaction that sufficiently solubilizes the reactants to afford a medium within which to effect the desired reaction.

The terms and abbreviations used in the instant Preparations and Examples have their normal meanings unless otherwise designated. For example, as used herein, the following terms have the meanings indicated: "eq" refers to equivalents; "N" refers to normal or normality; "M" refers to molar or molarity; "g" refers to gram or grams; "mg" refers to milligrams; "L" refers to liters; "mL" refers to milliliters; "µL" refers to microliters; "mol" refers to moles; "mmol" refers to millimoles; "psi" refers to pounds per square inch; "min"

refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "SCX chromatography" refers to strong cation exchange chromatography; "δ" refers to part per million down-field from tetramethylsilane; "MS" refers to mass spectrometry; Observed Mass indicates (M+1) unless indicated otherwise; "MS(FD)" refers to field desorption mass spectrometry; "MS (IS)" refers to ion spray mass spectrometry; "MS(FIA)" refers to flow injection analysis mass spectrometry; "MS (FAB)" refers to fast atom bombardment mass spectrometry; "MS(EI)" refers to electron impact mass spectrometry; "MS (ES)" refers to electron spray mass spectrometry; "UV" refers to ultraviolet spectrometry; "1H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

"Boc" or "BOC" refers to t-butyl carbamate. "HOBt" is 1-hydrobenzotriazole. "PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine. "EDC" is 1-Ethyl-3-[3-dimethylaminopropyl]carbodiimide hydrochloride. "HATU" is O-(7-azabenzotriazol-1-yl)-N-N-N'-N'-tetramethyluronium hexafluorophosphate. "TBTU" is 1H-Benzotriazolium, 1-[bis(dimethylamino)methylene]-, tetrafluoroborate(1-),3-oxide O-(Benzotriazol-1-yl)-N,N,N', N'-tetramethyluronium tetrafluoroborate. "THF" is tetrahydrofuran. "DMF" is dimethylformamide. "EtOH" is ethyl alcohol or ethanol. "EtOAc" is ethyl acetate. "DIEA" is diisopropylethyl amine. "MeOH" is methyl alcohol or methanol. "DCC" is dicyclohexylcarbodiimide. "DME" is ethylene glycol dimethyl ether. "DEAD" is diethyl azodicarboxylate. "DIAD" is diisopropyl azodicarboxylate.

In one embodiment, the present invention provides compounds of Formula I as described in detail above. While all of the compounds of the present invention are useful, certain of the compounds are particularly interesting and are preferred.

In a preferred embodiment the invention provides a compound structurally represented by Formula I, or a pharmaceutically acceptable salt thereof, wherein one occurrence of R6 is —H, and the second occurrence of R6 is —($C_1$-$C_3$) alkyl (optionally substituted with one to three halogens).

In another preferred embodiment the invention provides a compound structurally represented by Formula I, or a pharmaceutically acceptable salt thereof, wherein one occurrence of R6 is —H, and the second occurrence of R6 is —$CH_3$.

In another preferred embodiment the invention provides a compound structurally represented by Formula I, or a pharmaceutically acceptable salt thereof, wherein:

R1 is independently

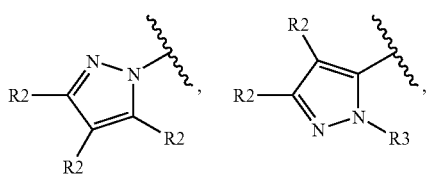

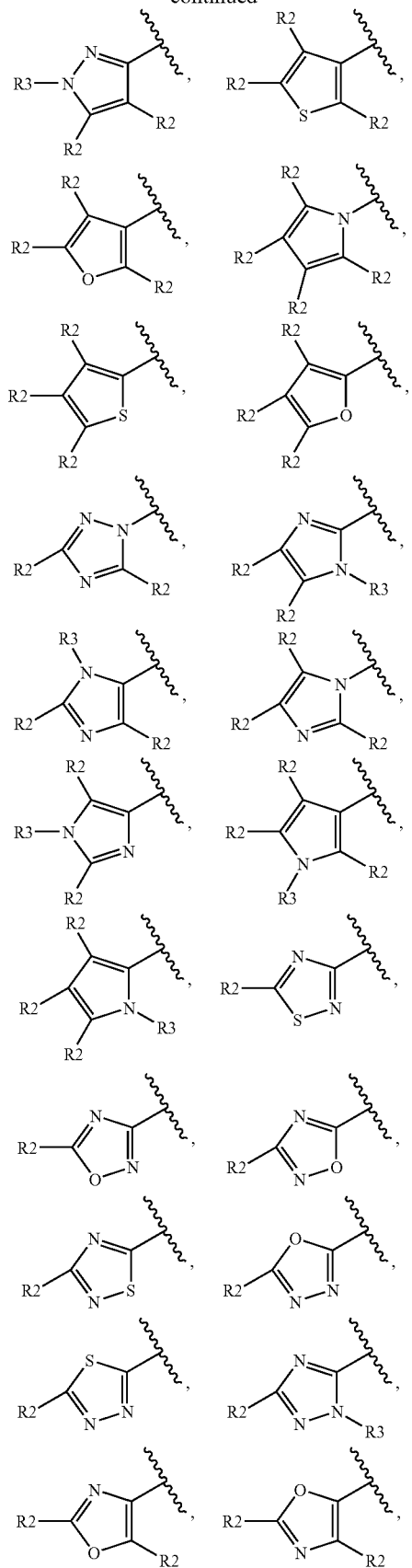

-continued

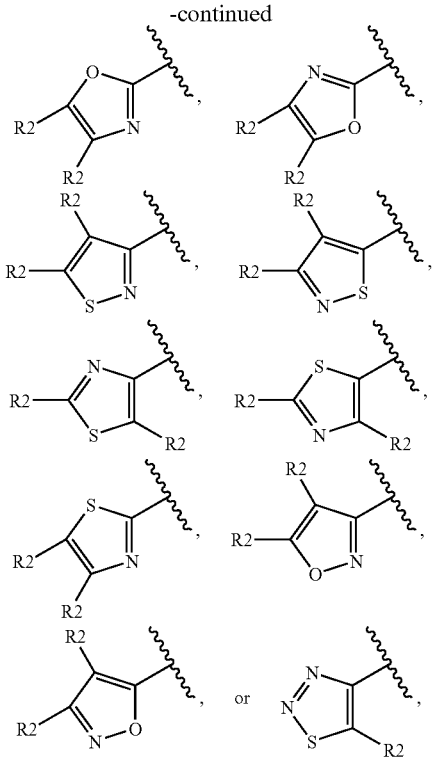

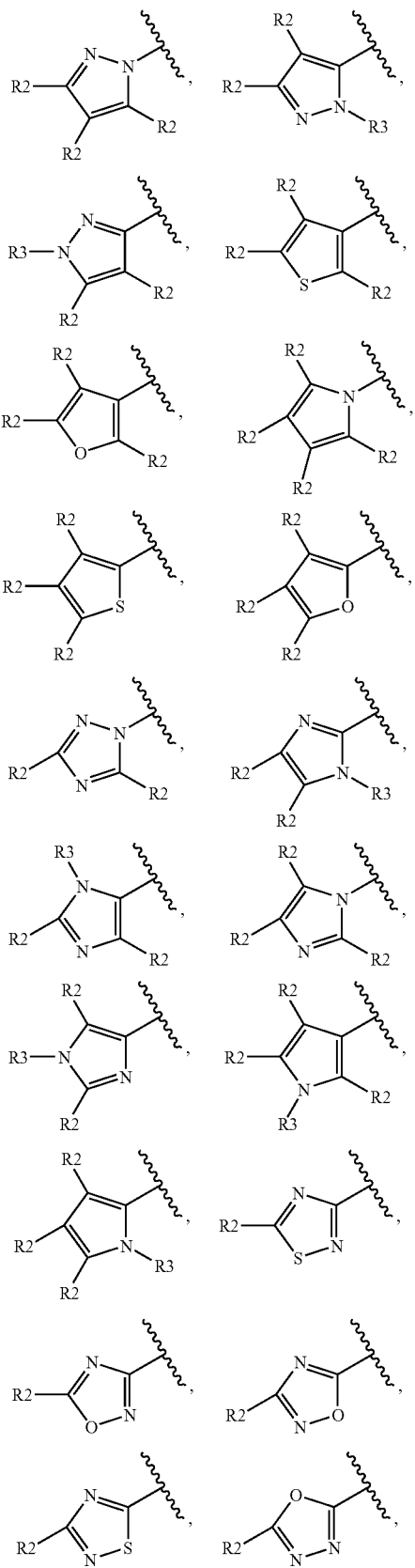

wherein the bond directed to the zig-zag lines indicates the point of attachment to the position indicated by R1 in Formula I;

R2 is independently at each occurrence
—H, -halogen, —($C_1$-$C_3$) alkyl (optionally substituted with one to three halogens), —CN, —C(O)R7, —C(O)OR7, —CO(O)Li, —C(O)($C_3$-$C_5$)cycloalkyl, —C(O)NR7R8, —OCF$_3$, —OR7, —NO$_2$, —NR7R8, —NR9SO$_2$R7, —NR9C(O)R7, —NR9CO$_2$R7, —NR9C(O)NR7R8, —SR7, —SO$_2$R7, —SO$_2$CF$_3$, —SO$_2$NR7R8, or —S(O)R7;

R3 is independently at each occurrence
—H, —($C_1$-$C_3$) alkyl (optionally substituted with one to three halogens), —SO$_2$R7, —C(O)R7, —C(O)NR7R8, or —C(O)OR7;

R4 and R5 are independently
—H, —OH, -halogen, —($C_1$-$C_3$) alkyl (optionally substituted with one to three halogens), or —OR9;

R6 is independently at each occurrence
—H, -halogen, —($C_1$-$C_3$) alkyl (optionally substituted with one to three halogens), —NH$_2$, —NR7R8, —OH, or —OR7;

R7 and R8 are independently at each occurrence
—H, or —($C_1$-$C_7$) alkyl (optionally substituted with one to three halogens), wherein R7 and R8 can combine with the atom to which they are attached to form a four to six membered ring; and R9 is independently at each occurrence
—H or —($C_1$-$C_3$) alkyl (optionally substituted with one to three halogens).

In another preferred embodiment the invention provides a compound structurally represented by Formula I, or a pharmaceutically acceptable salt thereof, wherein:

R1 is independently

-continued

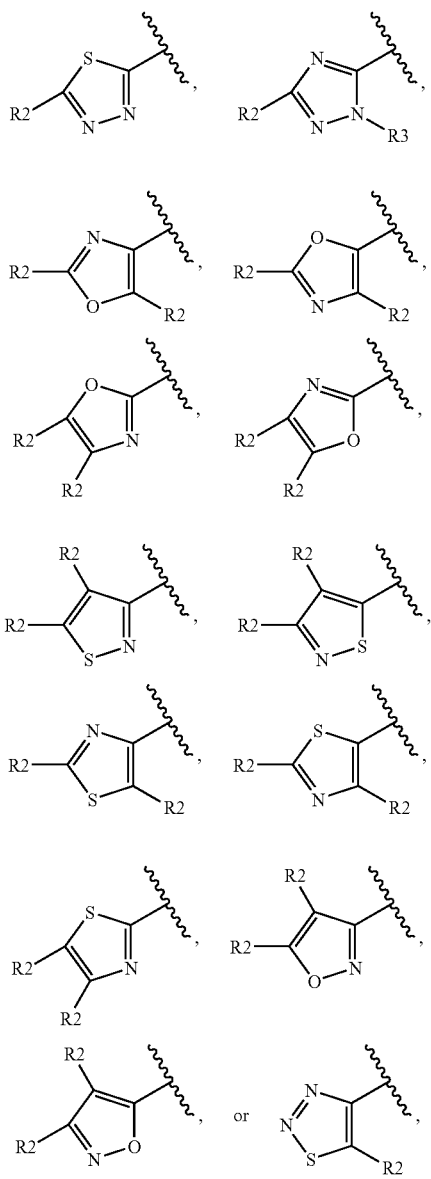

wherein the bond directed to the zig-zag lines indicates the point of attachment to the position indicated by R1 in Formula I;

R2 is independently at each occurrence
— H, -halogen, —($C_1$-$C_3$) alkyl (optionally substituted with one to three halogens), or —CN;

R3 is independently at each occurrence
— H or —($C_1$-$C_3$) alkyl (optionally substituted with one to three halogens);

R4 and R5 are independently —H or -halogen; and

One occurrence of R6 is —H, and the second occurrence of R6 is independently —H, -halogen, or —($C_1$-$C_3$) alkyl (optionally substituted with one to three halogens).

In another preferred embodiment the invention provides a compound structurally represented by Formula I, or a pharmaceutically acceptable salt thereof, wherein:

R1 is independently

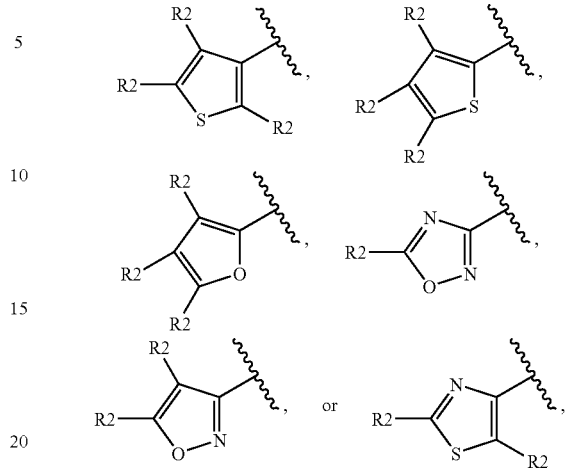

wherein the bond directed to the zig-zag lines indicates the point of attachment to the position indicated by R1 in Formula I;

R2 is independently at each occurrence
— H, -halogen, —($C_1$-$C_3$) alkyl (optionally substituted with one to three halogens), or —CN;

R3 is independently at each occurrence
— H or —($C_1$-$C_3$) alkyl (optionally substituted with one to three halogens);

R4 and R5 are independently —H or -halogen; and

One occurrence of R6 is —H, and the second occurrence of R6 is independently —H, -halogen, or —($C_1$-$C_3$) alkyl (optionally substituted with one to three halogens).

In another preferred embodiment the invention provides a compound structurally represented by Formula I, or a pharmaceutically acceptable salt thereof, wherein:

R1 is independently

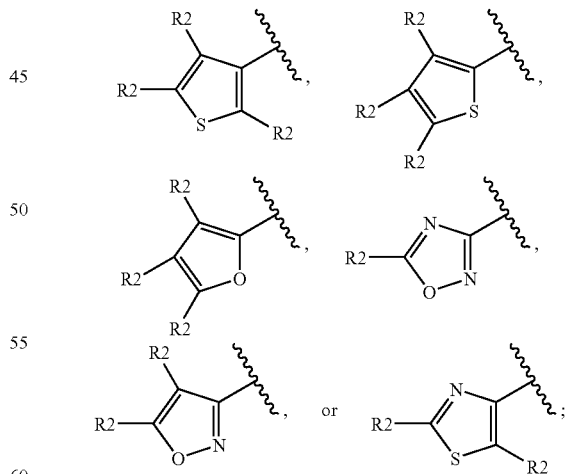

R2 is independently at each occurrence —H, —($C_1$-$C_3$) alkyl (optionally substituted with one to three halogens), or —CN; R4 is independently -hydrogen or -halogen and R5 is independently -halogen; Once occurrence of R6 is hydrogen, and the second occurrence of R6 is independently —H or —($C_1$-$C_3$) alkyl (optionally substituted with one to three halogens).

In another embodiment the invention provides a compound structurally represented by Formula I, or a pharmaceutically acceptable salt thereof, wherein:

R1 is independently

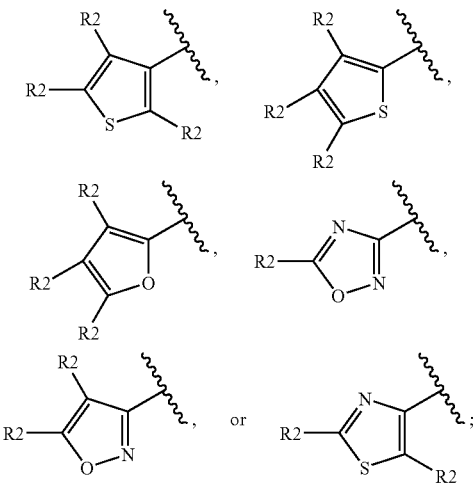

R2 is —H, —CH$_3$, —CF$_3$, or —CN; R4 is -hydrogen or —F; R5 is -hydrogen or —F; One occurrence of R6 is —H, and the second occurrence of R6 is —H or —CH$_3$.

The following listing sets out several additional groups of preferred embodiments. It will be understood that each of the listings may be combined with the embodiments described above to create additional groups of preferred embodiments. Thus, in additional preferred embodiments, the invention provides a compound structurally represented by the formulae of the above embodiments, or a pharmaceutically acceptable salt thereof:

1. wherein R1 is selected from the group consisting of

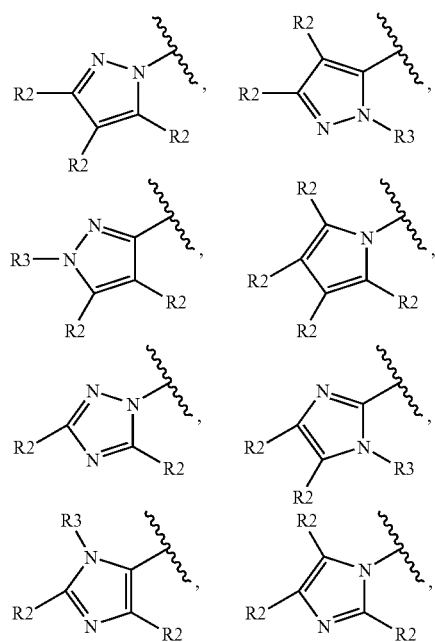

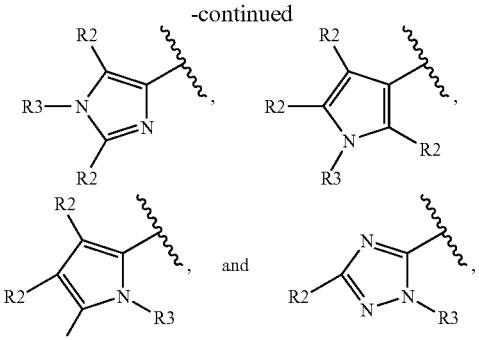

wherein the bond directed to the zig-zag lines indicates the point of attachment to the position indicated by R1 in Formula I.

2. wherein R1 is selected from the group consisting of

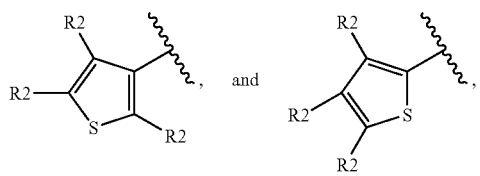

wherein the bond directed to the zig-zag lines indicates the point of attachment to the position indicated by R1 in Formula I.

3. wherein R1 is selected from the group consisting of

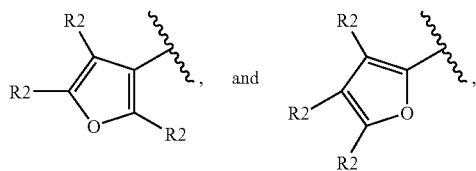

wherein the bond directed to the zig-zag lines indicates the point of attachment to the position indicated by R1 in Formula I.

4. wherein R1 is selected from the group consisting of

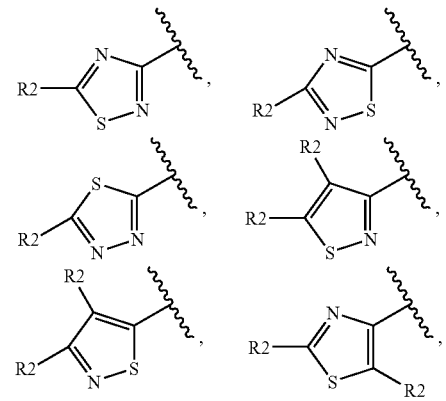

-continued

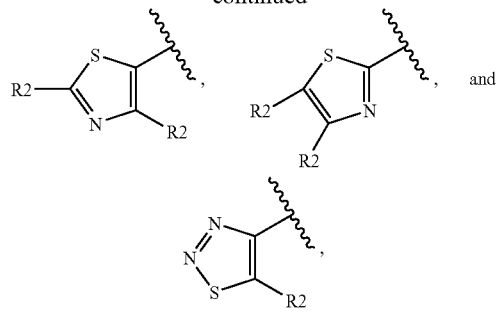

wherein the bond directed to the zig-zag lines indicates the point of attachment to the position indicated by R1 in Formula I.

5. wherein R1 is selected from the group consisting of

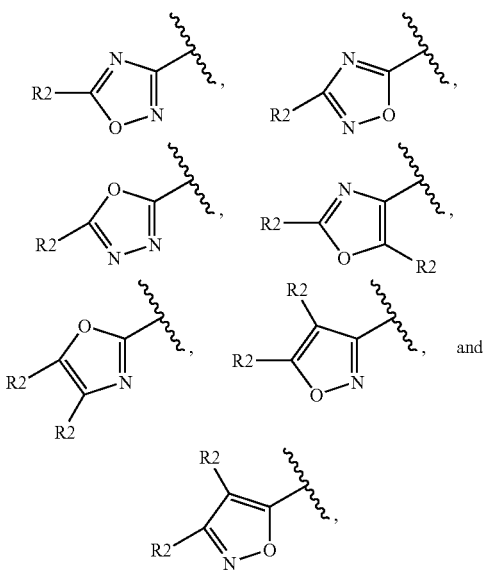

wherein the bond directed to the zig-zag lines indicates the point of attachment to the position indicated by R1 in Formula I.

6. wherein R2 is selected from the group consisting of hydrogen, —($C_1$-$C_7$) alkyl (optionally substituted with one to three halogens), and —CN.
7. wherein R2 is selected from the group consisting of hydrogen, —$CH_3$, —$CF_3$, and —CN.
8. wherein R4 is hydrogen or -halogen.
9. wherein R4 is hydrogen or —F.
10. wherein R5 is hydrogen or -halogen.
11. wherein R5 is hydrogen or —F.
12. wherein R4 is -hydrogen and R5 is -hydrogen or -halogen.
13. wherein R4 is -hydrogen and R5 is -hydrogen or —F.
14. wherein R6 is hydrogen or —($C_1$-$C_3$) alkyl (optionally substituted with one to three halogens).
15. wherein R6 is hydrogen or —$CH_3$.

In another preferred embodiment the invention provides a compound structurally represented by Formula II:

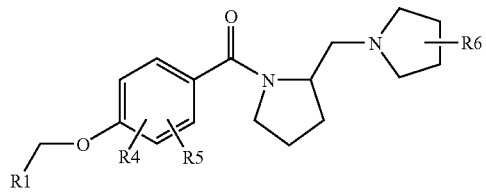

or a pharmaceutically acceptable salt thereof wherein:
R1 is independently

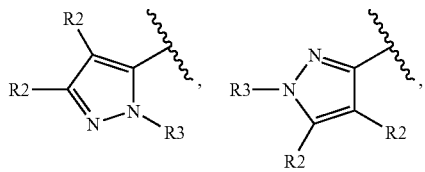
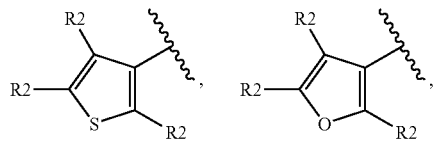
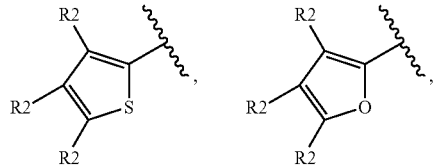
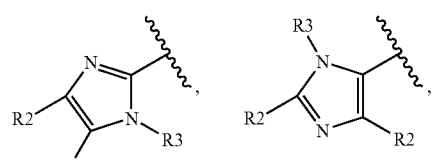
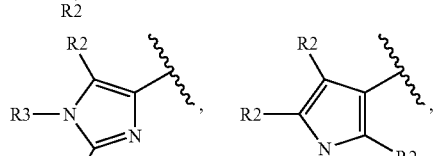
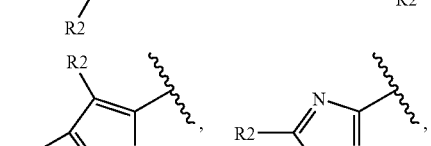
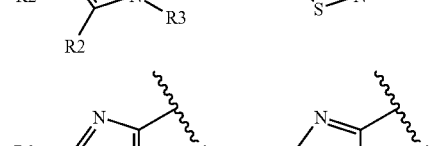
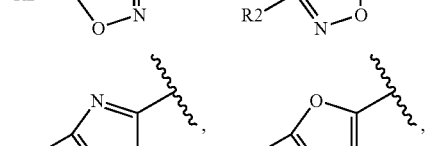

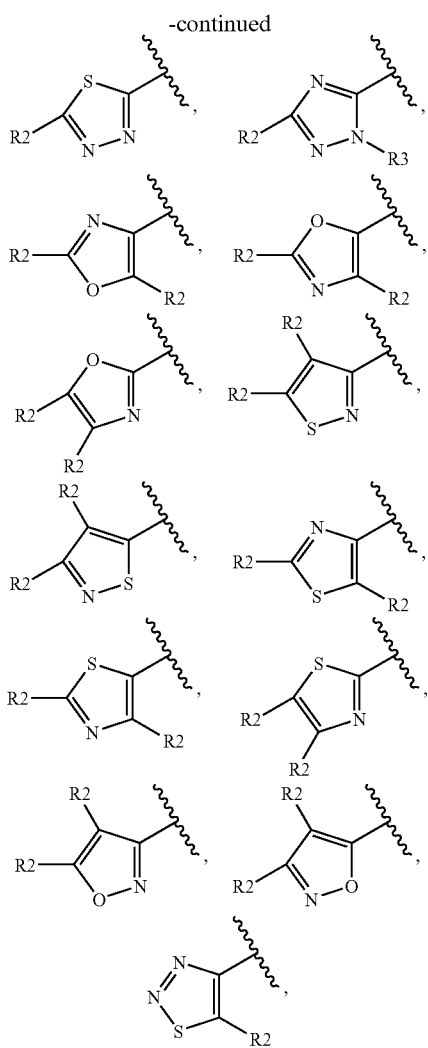

wherein the bond directed to the zig-zag lines indicates the point of attachment to the position indicated by R1 in Formula I, R2 is independently at each occurrence
—H, -halogen, —($C_1$-$C_7$) alkyl (optionally substituted with one to three halogens), —CN, —C(O)R7, —C(O)OR7, —CO(O)Li, —C(O)($C_3$-$C_5$)cycloalkyl, —C(O)NR7R8, —OCF$_3$, —OR7, —NO$_2$, —NR7R8, —NR9SO$_2$R7, —NR9C(O)R7, —NR9CO$_2$R7, —NR9C(O)NR7R8, —SR7, —SO$_2$R7, —SO$_2$CF$_3$, —SO$_2$NR7R8, —S(O)R7;

R3 is independently at each occurrence
—H, —($C_1$-$C_7$) alkyl (optionally substituted with one to three halogens), -phenyl, -benzyl, —SO$_2$R7, —C(O)R7, —C(O)NR7R8, —C(O)OR7;

R4 and R5 are independently at each occurrence
—H, —OH, -halogen, —($C_1$-$C_3$) alkyl (optionally substituted with one to three halogens), —OR9;

R6 is independently at each occurrence
—H, -halogen, —($C_1$-$C_3$) alkyl (optionally substituted with one to three halogens), —NH$_2$, —NR7R8, —OH, —OR7;

R7 and R8 are independently at each occurrence
—H, —($C_1$-$C_7$) alkyl (optionally substituted with one to three halogens);
wherein R7 and R8 can combine with the atom to which they are attached to form a three to seven membered ring;

R9 is
—H, —($C_1$-$C_3$) alkyl (optionally substituted with one to three halogens).

In other preferred embodiments, the invention provides compounds structurally represented by Formulae X1 to X20, and pharmaceutically acceptable salts thereof:

| Formula Number | Structure |
|---|---|
| X1 | 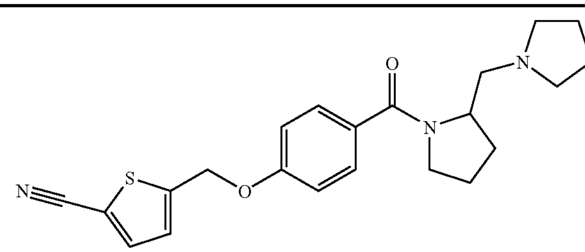 |
| X2 | 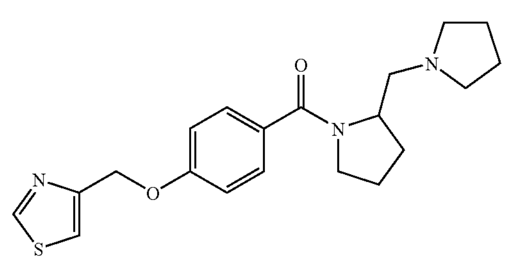 |

-continued
| Formula Number | Structure |
|---|---|
| X3 | 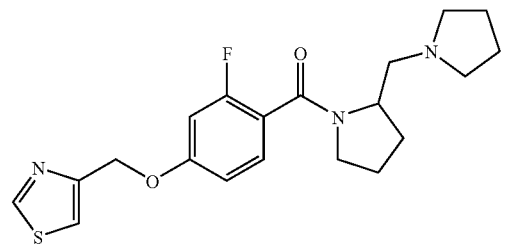 |
| X4 | 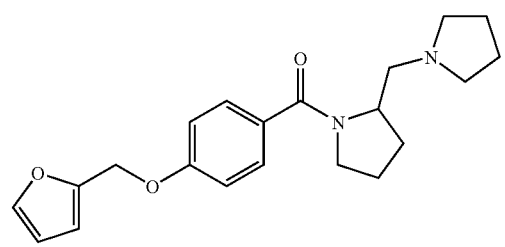 |
| X5 | 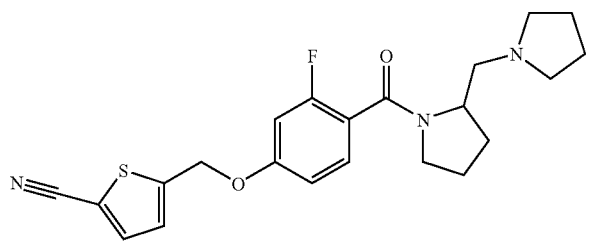 |
| X6 | 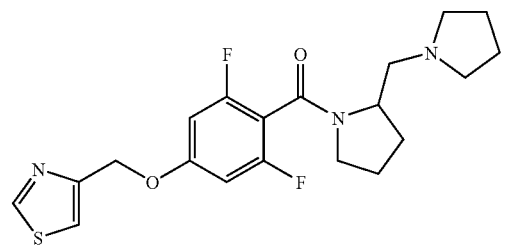 |
| X7 | 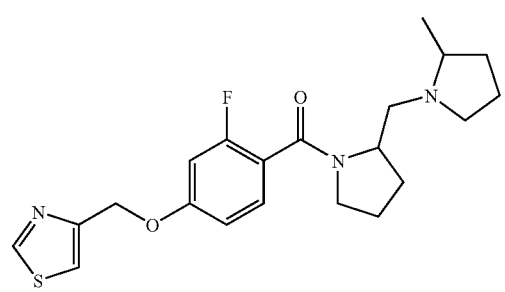 |
| X8 | 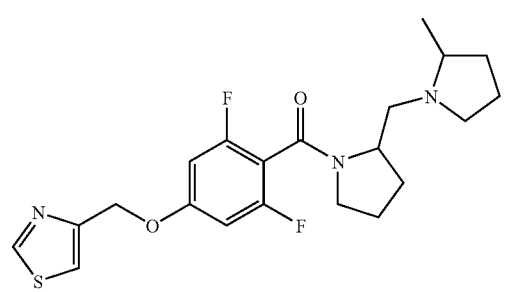 |

-continued
| Formula Number | Structure |
| --- | --- |
| X9 | 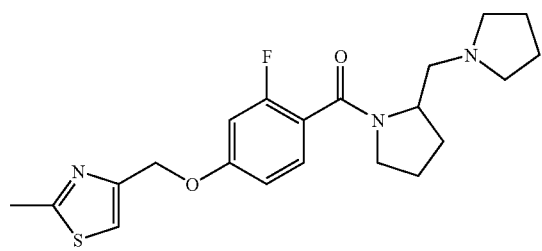 |
| X10 | 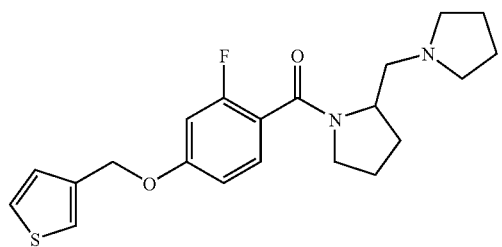 |
| X11 | 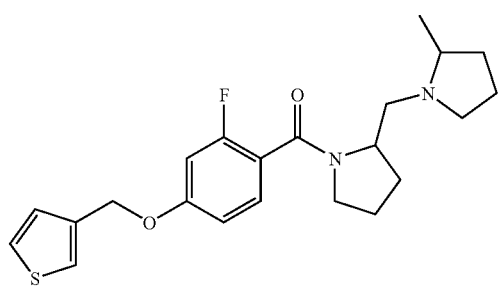 |
| X12 | 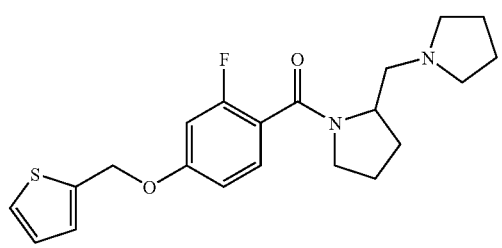 |
| X13 | 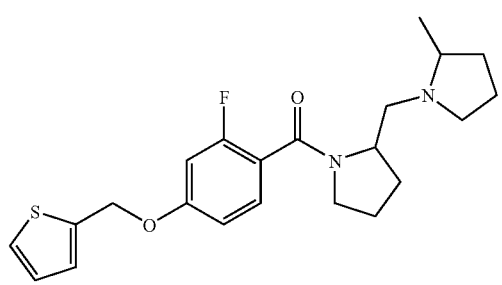 |

-continued
| Formula Number | Structure |
|---|---|
| X14 | 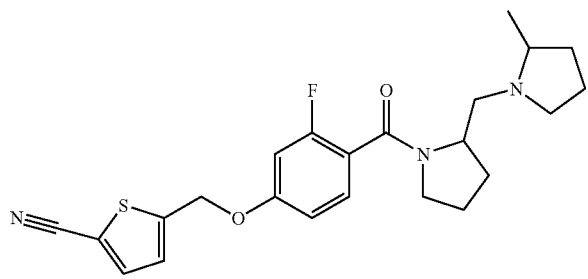 |
| X15 | 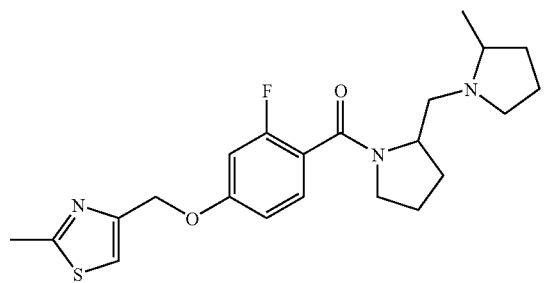 |
| X16 | 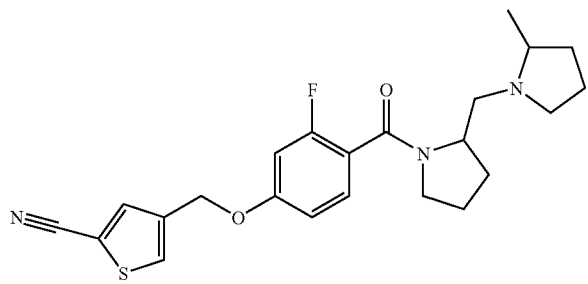 |
| X17 | 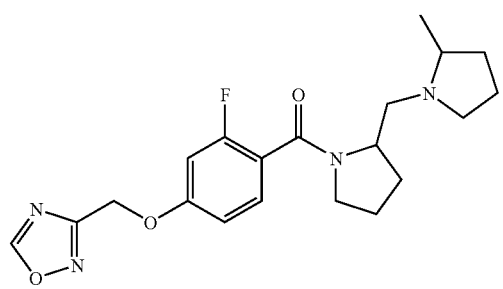 |
| X18 | 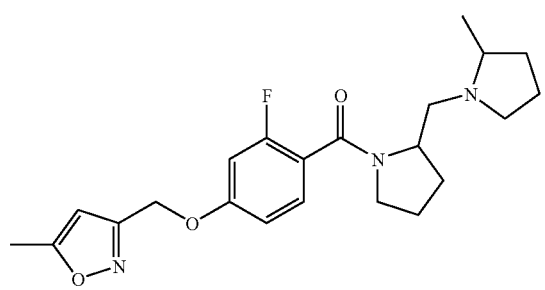 |

-continued

| Formula Number | Structure |
|---|---|
| X19 | 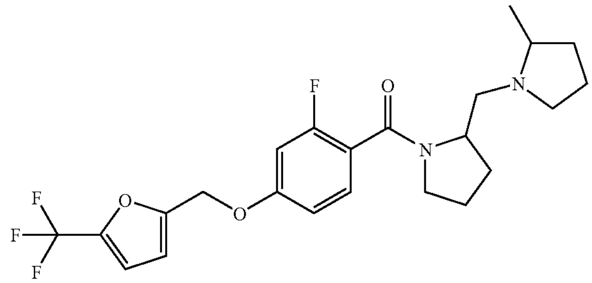 |
| X20 | 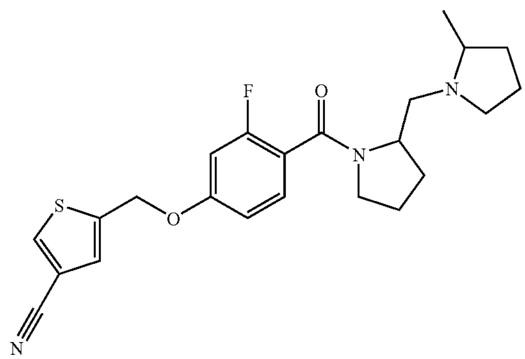 |

Due to their interaction with the histamine H3 receptor, the present compounds are useful in the treatment of a wide range of conditions and disorders in which an interaction with the histamine H3 receptor is beneficial. Thus, the compounds may find use for example to prevent, treat and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders which include but are not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like.

The present invention also provides a pharmaceutical composition which comprises a compound of Formula I or Formula II and a pharmaceutically acceptable carrier. Pharmaceutical formulations of Formula I or Formula II can provide a method of selectively increasing histamine levels in cells, or increasing histamine release by cells, by contacting the cells with an antagonist or inverse agonist of the histamine H3 receptor, the antagonist or inverse agonist being a compound of Formula I or Formula II. Thus, the methods of this invention encompass a prophylactic and therapeutic administration of a compound of Formula I or Formula II.

The present invention further provides an antagonist or inverse agonist of Formula I or Formula II which is characterized by having little or no binding affinity for the histamine receptor GPRv53.

Thus, a pharmaceutical preparation of Formula I or Formula II can be useful in the treatment or prevention of obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, which comprises administering to a subject in need of such treatment or prevention an effective amount of a compound of Formula I or Formula II. In addition, a pharmaceutical preparation of Formula I or Formula II can be useful in the treatment or prevention of a disorder or disease in which modulation of histamine H3 receptor activity has a beneficial effect or the treatment or prevention of eating disorders which comprises administering to a subject in need of such treatment or prevention an effective amount of a compound of Formula I or Formula II. In yet another aspect, the present invention provides compounds, pharmaceutical compositions, and methods useful in the treatment of nervous system and other disorders associated with histamine H3 receptor.

In addition, the present invention relates to a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity; and for use in treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo. Thus, the uses and methods of this invention encompass a prophylactic and therapeutic administration of a compound of Formula I or II.

The present invention is further related to the use of a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

The present invention further provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formula I or II or a pharmaceutically acceptable salt thereof, or a pharmaceutical composition which comprises a compound of Formula I or II, or a pharmaceutical salt thereof, and a pharmaceutically acceptable carrier, diluent, or excipient.

The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formula I or II, or a pharmaceutical salt thereof, and a pharmaceutically acceptable carrier, diluent, or excipient. In addition, a pharmaceutical composition of Formula I or II can be useful in the treatment or prevention of a disorder or disease in which modulation of histamine H3 receptor activity has a beneficial effect. The present invention further provides an antagonist or inverse agonist of Formula I or II which is characterized by having greater affinity for the histamine H3 receptor as compared to the affinity for the histamine H1R, H2R, or H4R receptors. In addition the embodiments of the present invention include the synthesis of the examples named herein by methods included herein, and supplemented by methods known in the art, to create positron emission topography (PET) ligands that bind to histamine H3 receptors and are useful for PET imaging.

The invention includes tautomers, enantiomers, and other stereoisomers of the compounds. Thus, as one skilled in the art knows, certain aryls may exist in tautomeric forms. Such variations are contemplated to be within the scope of the invention. It will be understood that, as used herein, references to the compounds of Formula I or Formula II are meant to also include enantiomers and racemic mixtures, and the pharmaceutical salts thereof.

As used herein, the term "stereoisomer" refers to a compound made up of the same atoms bonded by the same bonds but having different three-dimensional structures. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} X 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or Formula II can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers, and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ▬ " refers to a bond that protrudes forward out of the plane of the page. The designation " ⋯⋯ " refers to a bond that protrudes backward out of the plane of the page. The designation " ∼ " refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I or Formula II which are substantially non-toxic to living organisms. See, e.g., Berge, S. M, Bighley, L. D., and Monkhouse, D. C., "Pharmaceutical Salts," *J. Pharm. Sci.*, 66:1, 1977. Typical pharmaceutical salts include those salts prepared by reaction of the compounds of Formula I or Formula II with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or Formula II prepared by reaction of a compound of Formula I or Formula II with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I or Formula II with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I or Formula II prepared by reaction of a compound of Formula I or Formula II with a mineral or organic base. For exemplification of pharmaceutical base addition salts see, e.g., Berge, S. M, Bighley, L. D., and Monkhouse, D. C., *J. Pharm. Sci.*, 66:1, 1977. The present invention also contemplates pharmaceutical base addition salts of compounds of Formula I or Formula II. The skilled artisan would appreciate that some compounds of Formula I or Formula II may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I or Formula II.

The compounds of Formula I or Formula II, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I or Formula II may be obtained by stereospecific synthesis using optically pure starting materials or reagents of known configuration or through enantioselective synthesis.

The compounds of Formula I or Formula II can be prepared by one of ordinary skill in the art following a variety of procedures, some of which are illustrated in the procedures and schemes set forth below. The particular order of steps required to produce the compounds of Formula I or Formula II is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

Compounds of the present invention have been formed as specifically described in the examples. Further, many compounds are prepared using the general schemes described below. Unless otherwise indicated, all variables are defined as herein, and as defined for analogously positioned variables in the summary of the invention. Alternative methods of synthesis may also be effective and known to the skilled artisan.

General Preparations:

SCHEME A

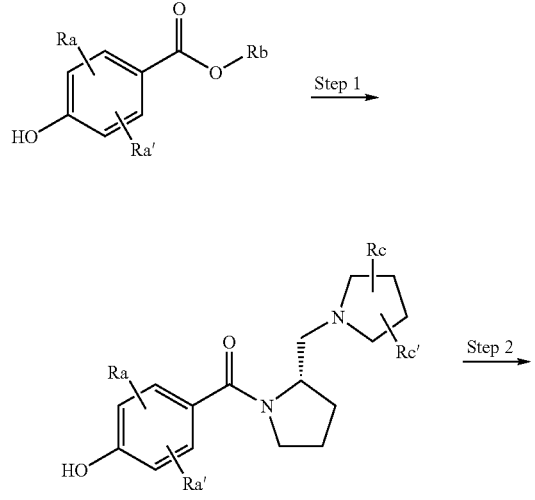

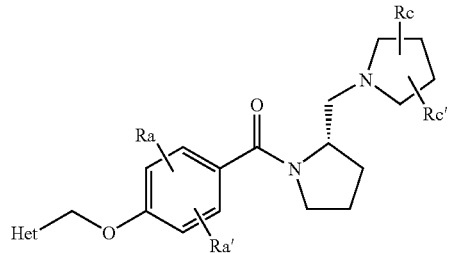

In Scheme A, $R_a$ and $R_{a'}$ are each independently but not limited to F, Cl, $CF_3$, alkyl and can include disubstituted compounds; $R_b$ is H, or the corresponding carboxylic acids salts; $R_c$ and $R_{c'}$ are each independently but not limited to alkyl, amino, hydroxy, and Het is any 5-membered heteroaromatic ring including but not limited to furan, imidazole, isothiazole, isoxazole, oxadiazole, oxazole, pyrazole, pyrrole, tetrazole, thiadiazole, thiazole, thiophene and triazole. In Scheme A, Step 1, aryl carboxylic acids, or the lithium, sodium, or potassium salt of the acid, where $R_b$ can be H, Li, Na, or K are converted to the corresponding amides using a number of different methods known in the literature. Some of these methods can be found described in a review of coupling reagents in peptide synthesis by Klausner & Bodansky, Synthesis, 1972, 9, 453-463.

For example, 4-hydroxybenzoic acid or the corresponding lithium or sodium salt is suspended a suitable organic solvent such as dichloromethane, DMF, or mixtures thereof. A suitable amide coupling agent i.e EDC, DCC, TBTU, etc., is added followed by HOBt, HATU, etc., at room temperature. Diisopropylethyl amine and suitable amine in this case, (S) (+)-1-(2-pyrrolidinylmethyl)pyrrolidine, are added to the mixture. The mixture is stirred at room temperature for a period of 8-48 hours. The reaction is quenched by addition of water. The resulting mixture may be extracted, concentrated, and purified according to techniques well known in the art.

Alternatively the corresponding acid chloride can be formed from the corresponding acid, or salt thereof, using thionyl chloride or oxalyl chloride and a few drops DMF, and treated with a suitable amine to give the desired amide.

In Scheme 1, Step 2, the phenols are converted to the ethers by alkylation with alkyl bromides, chlorides, iodides, mesylates, tosylate, etc., with a suitable base such as $Cs_2CO_3$, $K_2CO_3$, or triethylamine, etc., in a suitable solvent such as DMF, acetone, THF or $CH_2Cl_2$. The alkylation is carried out at room temperature or with heating.

For example, (4-hydroxy-phenyl)-(2-(S)-pyrrolidin-1-yl-methyl-pyrrolidin-1-yl)-methanone, where Ra, Ra'=H, and $Cs_2CO_3$, are suspended in DMF and 5-bromomethyl-thiophene-2-carbonitrile is added. The mixture is stirred at room temperature for 24-48 h. After an aqueous workup, the crude material may be purified by well known techniques.

Alternatively the ether can be formed by a Mitsunobu, or related reaction, using an alkyl alcohol and a coupling agent such as DEAD, DIAD, etc., with triphenyl phosphine in a suitable solvent such as THF or $CH_2Cl_2$. The reaction is quenched with water, and the resulting mixture may be extracted, concentrated, and purified according to techniques well known in the art.

SCHEME B

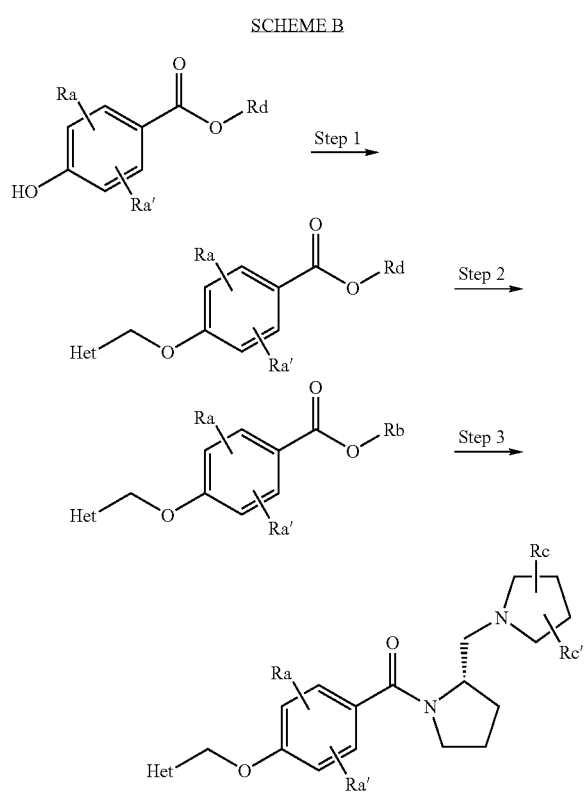

In Scheme B, $R_a$, $R_{a'}$, $R_b$, $R_c$ $R_{c'}$, and Ar are as defined herein. $R_d$ can be Methyl, Ethyl, Benzyl, or butyl esters. In Scheme B (step 1), the carboxylic acid esters are alkylated by the methods described in Scheme A (step 2).

For example, 2-fluoro-4-hydroxy-benzoic acid methyl ester, 5-bromomethyl-thiophene-2-carbonitrile, and $K_2CO_3$ in acetone are heated at reflux for 5 h. The mixture is cooled to room temperature and filtered. The solvent is removed to provide the ether which can be purified by well known techniques or in some cases used without purification.

In addition, the ether can be formed by a Mitsunobu or related reaction using an alkyl alcohol and a coupling agent such as DEAD, DIAD, etc., with triphenyl phosphine in a suitable solvent such as THF or $CH_2Cl_2$. The reaction is quenched with water, and the resulting mixture may be extracted, concentrated, and purified according to techniques well known in the art.

For example, to a mixture of 2-fluoro-4-hydroxy-benzoic acid methyl ester, furfuryl alcohol, and triphenylphosphine, in a suitable solvent such as THF, is added DIAD. The mixture is stirred at room temperature overnight. The resulting mixture may be extracted, concentrated, and purified according to techniques well known in the art.

In Scheme B, Step 2, the resulting esters (wherein $R_e$=Methyl, Ethyl, Benzyl, etc.), can be saponified using standard conditions to yield the corresponding carboxylic acids, or the lithium, sodium, or potassium salt of the acid, where $R_b$ can be H, Li, Na, or K. For example, to a mixture of 2-fluoro-4-(thiazol-4-ylmethoxy)-benzoic acid methyl ester in dioxane is added a solution of lithium hydroxide monohydrate in $H_2O$. The mixture is stirred at room temperature for 24-48 h. The solvent is removed in vacuo to provide the crude lithium salt which can be used without further purification.

In Scheme B, Step 3, the acids or the corresponding lithium, sodium, or potassium salts (wherein $R_b$=H, Li, Na, K) are converted to the pyrrolidinylmethylpyrrolidine amides by the methods described in Scheme A (step 1).

Intermediate Preparation 1

(4-Hydroxy-phenyl)-(2-(S)-pyrrolidin-1-ylmethyl-pyrrolidin-1-yl)-methanone

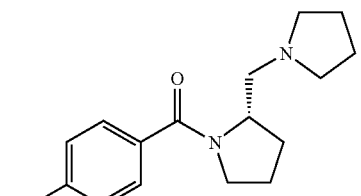

Procedure A:

4-hydroxybenzoic acid (13.5 g, 97.9 mmol) is suspended in dichloromethane (400 mL). EDC (20.0 g, 104.3 mmol) and HOBt (14.1 g, 104.3 mmol) are added at room temperature in that order. DIEA (28.4 mL, 163 mmol) and (S)(+)-1-(2-pyrrolidinylmethyl)pyrrolidine (10.0 g, 65.2 mmol) are added to the mixture. The mixture is stirred at room temperature overnight. Water and ethyl acetate are added to the mixture. The product is water soluble necessitating a number of organic washes. The combined organic layers are dried over $Na_2SO_4$ and evaporated. The crude product is purified by silica-gel column chromatography (gradient: 100% $CH_2Cl_2$ to 10% 2M $NH_3$ in $MeOH/CH_2Cl_2$) to give the desired product (52%). MS(ES+): m/e 275; $^1$H-NMR ($CDCl_3$): 7.29 (bm, 2H), 6.76 (d, 2H), 4.50 (m, 1H), 3.52 (m, 2H), 2.90 (bm, 1H), 2.70 (bm, 4H), 2.04 (bm, 1H), 1.95 (bm, 2H), 1.67 (bm, 6H).

Intermediate Preparation 2

2-(R)-Methyl-1-(2-(S)-pyrrolidinylmethyl)pyrrolidine

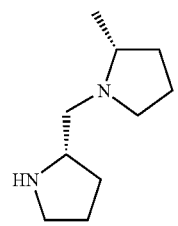

(S) BOC proline (CAS 15761-39-4) and 2-(R)-methyl-pyrrolidine hydrochloride (CAS 135324-85-5) are coupled in a manner substantially analogous to Procedure A in dichloromethane to give 2(S)-(2(R)-methyl-pyrrolidine-1-carbonyl)-pyrrolidine-1-carboxylic acid tert-butyl ester. The material is deprotected by stirring in dichloromethane at 5-10° C. while trifluoroacetic acid (10 eq,) is added and then stirred at room temperature for 18 hours. The reaction is concentrated and is dissolved in $H_2O$. The pH is adjusted to 8-9 with $K_2CO_3$, and is extracted several times with $CH_2Cl_2$. The extracts are combined, dried ($Na_2SO_4$) and concentrated in vacuo to give (2(R)-methyl-pyrrolidin-1-yl)-pyrrolidin-2-yl-methanone. A 1 M lithium aluminum hydride/THF solution (3 eq.) is diluted with an equal volume of THF and stirred under $N_2$ as a THF solution of (2(R)-methyl-pyrrolidin-1-yl)-pyrrolidin-2-yl-methanone is added dropwise, allowing the reaction to mildly exotherm. Reaction is stirred at 40° C. for 45 minutes, then at room temperature 18 hours. Reaction is cooled in an ice bath and is quenched with $H_2O$ (3 eq.), 4 N NaOH (3 eq.), and $H_2O$ (9 eq.) maintaining the reaction temperature less than 15° C. The reaction is stirred overnight, filtered, and the precipitate is washed three times with THF. The filtrate and washes are combined and concentrated to give 2-(R)-methyl-1-(2-(S)-pyrrolidinylmethyl)pyrrolidine. MS (ES+) m/e 169.3 (M+H)+ Intermediate is used as such or is purified by SCX chromatography or distillation.

Intermediate Preparation 3

(2-Fluoro-4-hydroxy-phenyl)-[2-(S)-(2-(R)-methyl-pyrrolidin-1-ylmethyl)pyrrolidin-1-yl]-methanone

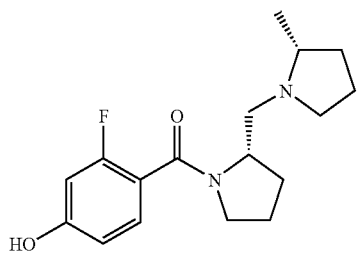

The title compound is prepared in a manner substantially analogous to Procedure A from 2-Fluoro-4-hydroxy-benzoic acid and 2-(R)-methyl-1-(2-(S)-pyrrolidinylmethyl)pyrrolidine. MS (ES+) m/e 307.3.

Intermediate Preparation 4

(2-Fluoro-4-hydroxy-phenyl)-(2-(S)-pyrrolidin-1-ylmethyl-pyrrolidin-1-yl)-methanone

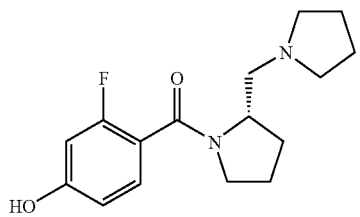

The title compound is prepared in a manner substantially analogous to Procedure A from 2-fluoro-4-hydroxybenzoic acid [CAS 65145-13-3] and (S)(+)-1-(2-pyrrolidinylmethyl) pyrrolidine. MS (ES+) m/e 293.1

EXAMPLE 1

5-[4-(2-(S)-Pyrrolidin-1-ylmethyl-pyrrolidine-1-carbonyl)-phenoxymethyl]-thiophene-2-carbonitrile

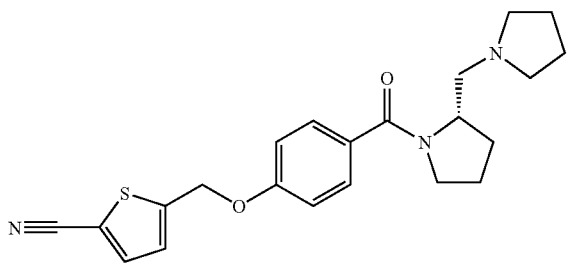

Procedure B:

A mixture of (4-hydroxy-phenyl)-(2-(S)-pyrrolidin-1-ylmethyl-pyrrolidin-1-yl)-methanone (145 mg, 0.53 mmol), $Cs_2CO_3$ (0.34 g, 1.06 mmol), and 5-bromomethyl-thiophene-2-carbonitrile [CAS 134135-41-4] (0.13 g, 0.64 mmol) in DMF (5 mL) is stirred at room temperature overnight. The mixture is partitioned between EtOAc and $H_2O$. The aqueous phase is extracted with EtOAc (2×). The combined organic phase is dried ($Na_2SO_4$) and concentrated. The crude product is purified by flash chromatography (40 g $SiO_2$, elute 20% (10% 2M $NH_3$ in MeOH/$CH_2Cl_2$)/80% $CH_2Cl_2$ to 70% (10% 2M $NH_3$ in MeOH/$CH_2Cl_2$)/30% $CH_2Cl_2$). MS (ES+) m/e 396.3

EXAMPLE 2

(2-(S)-Pyrrolidin-1-ylmethyl-pyrrolidin-1-yl)-[4-(thiazol-4-ylmethoxy)-phenyl]-methanone

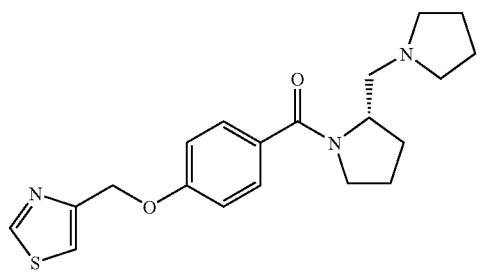

Procedure C:

A mixture of (4-Hydroxy-phenyl)-(2-(S)-pyrrolidin-1-ylmethyl-pyrrolidin-1-yl)-methanone (190 mg, 0.69 mmol), $Cs_2CO_3$ (0.45 g, 1.4 mmol), potassium iodide (166 mg, 1 mmol) and 4-(chloromethyl)thiazole hydrochloride [CAS 7709-58-2] (0.17 g, 1.0 mmol) in DMF (5 mL) is stirred at room temperature overnight. The mixture is partitioned between EtOAc and $H_2O$. The aqueous phase is extracted with EtOAc (2×). The combined organic phase is dried ($Na_2SO_4$) and concentrated. The crude product is purified by flash chromatography (40 g $SiO_2$, elute 20% (10% 2M $NH_3$ in MeOH/$CH_2Cl_2$)/80% $CH_2Cl_2$ to 70% (10% 2M $NH_3$ in MeOH/$CH_2Cl_2$)/30% $CH_2Cl_2$). MS (ES+) m/e 372.3

Intermediate Preparation 5

2-Fluoro-4-(thiazol-4-ylmethoxy)-benzoic acid methyl ester

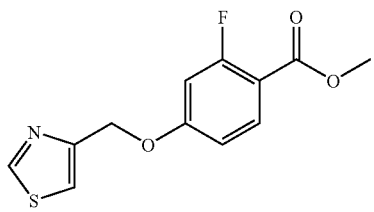

Procedure D:

A mixture of 2-fluoro-4-hydroxy-benzoic acid methyl ester [CAS 197507-22-5] (1.0 g, 5.9 mmol), 4-(chloromethyl)thiazole hydrochloride [CAS 7709-58-2] (1.3 g, 7.7 mmol), potassium carbonate (2.55 g, 20.6 mmol), and potassium iodide (0.98 g, 5.9 mmol) in acetone (30 mL) is heated at reflux overnight. The mixture is cooled to room temperature, filtered, and concentrated to dryness. The residue is partitioned between EtOAc and water. The aqueous phase is extracted with EtOAc (2×), and the combined organic phase is washed with brine, dried ($Na_2SO_4$), and concentrated. The residue is purified by flash chromatography (120 g $SiO_2$, elute gradient 100% $CH_2Cl_2$ to 50% (10% 2M $NH_3$ in MeOH/90% $CH_2Cl_2$)/50% $CH_2Cl_2$) to provide 0.49 g of the title compound. MS (ES+) m/e 268.0

EXAMPLE 3

[2-Fluoro-4-(thiazol-4-ylmethoxy)-phenyl]-(2-(S)-pyrrolidin-1-ylmethyl-pyrrolidin-1-yl)-methanone

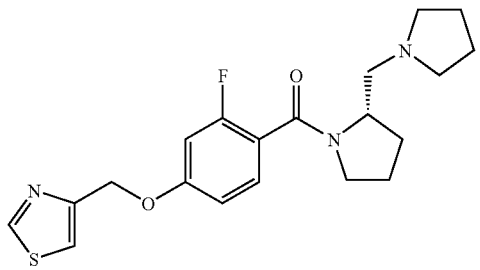

Procedure E:

To a mixture of 2-fluoro-4-(thiazol-4-ylmethoxy)-benzoic acid methyl ester (0.49 g, 1.8 mmol) in dioxane (20 mL) is added a solution of lithium hydroxide monohydrate (91 mg, 2.2 mmol) in water (5 mL). The mixture is stirred at room temperature overnight. The solvent is removed in vacuo and the crude lithium salt is used without purification.

To a mixture of 2-fluoro-4-(thiazol-4-ylmethoxy)-benzoic acid lithium salt (1.8 mmol) in $CH_2Cl_2$ (10 mL) and DMF (10 mL) is added EDC (0.41 g, 2.2 mmol), HOBt (0.29 g, 2.2 mmol), and DIEA (0.66 ml, 3.6 mmol). After a few minutes, (S)(+)-1-(2-pyrrolidinylmethyl)pyrrolidine (0.35 mL, 2.2 mmol) is added, and the mixture is stirred at room temperature overnight. The mixture is partitioned between water and ethyl acetate, and the aqueous phase is extracted with ethyl acetate (2×). The combined organic phase is dried ($Na_2SO_4$) and evaporated. The crude product is purified by flash chromatography (40 g $SiO_2$, elute 20% (10% 2M $NH_3$ in MeOH/$CH_2Cl_2$)/80% $CH_2Cl_2$ to 70% (10% 2M $NH_3$ in MeOH/$CH_2Cl_2$)/30% $CH_2Cl_2$) to yield 0.15 g of the title compound. MS (ES+) m/e 390.2

Intermediate Preparation 6

2-Fluoro-4-(furan-2-ylmethoxy)-benzoic acid methyl ester

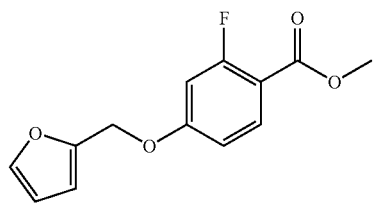

Procedure F:

To a mixture of 2-fluoro-4-hydroxy-benzoic acid methyl ester [CAS 197507-22-5] (0.25 g, 1.5 mmol) and furfuryl alcohol (0.19 mL, 2.2 mmol) are added triphenyl phosphine (0.58 mmol, 2.2 mmol) and diisopropyl azodicarboxylate (0.43 mL, 2.2 mmol). The mixture is stirred at room temperature overnight. The mixture is partitioned between EtOAc and $H_2O$. The aqueous phase is extracted with EtOAc (2×). The combined organic phase is washed with brine, dried ($Na_2SO_4$), and concentrated in vacuo. The crude product is purified by flash chromatography (40 g $SiO_2$, elute hexane to 30% EtOAc/hexane). MS (ES+) m/e 251.3

EXAMPLE 4

[4-(Furan-2-ylmethoxy)-phenyl]-(2-(S)-pyrrolidin-1-ylmethyl-pyrrolidin-1-yl)-methanone

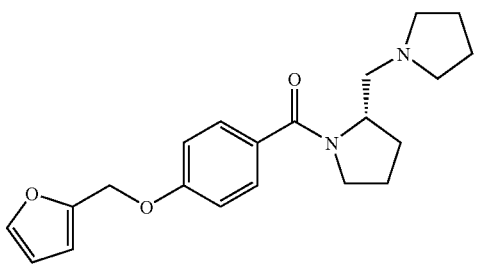

The title compound is prepared in a manner substantially analogous to Procedure E from 2-fluoro-4-(furan-2-ylmethoxy)-benzoic acid methyl ester. MS (ES+) m/e 373.3

EXAMPLE 5

5-[3-Fluoro-4-(2-(S)-pyrrolidin-1-ylmethyl-pyrrolidine-1-carbonyl)-phenoxymethyl]-thiophene-2-carbonitrile

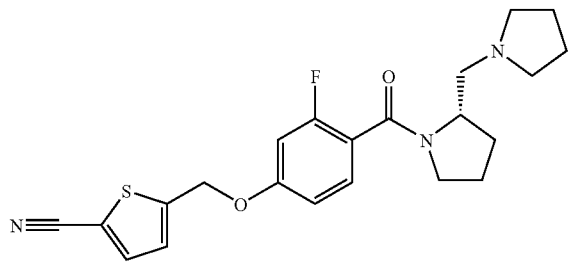

The title compound is prepared in a manner substantially analogous to Procedure B using (2-Fluoro-4-hydroxy-phenyl)-(2-(S)-pyrrolidin-1-ylmethyl-pyrrolidin-1-yl)-methanone and 5-bromomethyl-thiophene-2-carbonitrile [CAS 134135-41-4]. MS (ES+) m/e 414.2

EXAMPLE 6

[2,6-Difluoro-4-(thiazol-4-ylmethoxy)-phenyl]-(2-(S)-pyrrolidin-1-ylmethyl-pyrrolidin-1-yl)-methanone

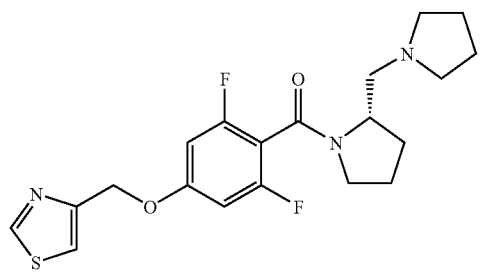

The title compound is prepared in a manner substantially analogous to Procedures D and E using 2,6-difluoro-4-hydroxy-benzoic acid methyl ester [CAS 194938-88-0], 4-(chloromethyl)thiazole hydrochloride [CAS 7709-58-2], and (S)(+)-1-(2-pyrrolidinylmethyl)pyrrolidine. MS (ES+) m/e 408.3

EXAMPLE 7

[2-Fluoro-4-(thiazol-4-ylmethoxy)-phenyl]-[2(S)-(2-(R)methyl-pyrrolidin-1-ylmethyl)-pyrrolidin-1-yl]-methanone

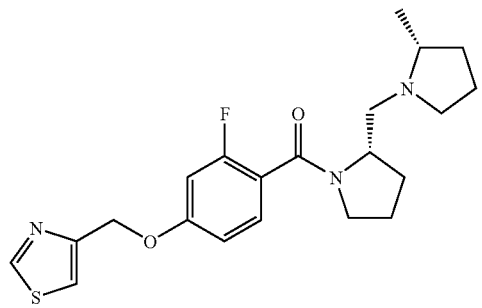

The title compound is prepared in a manner substantially analogous to Procedures D and E using 2-fluoro-4-hydroxy-benzoic acid methyl ester [CAS 197507-22-5], 4-(chloromethyl)thiazole hydrochloride [CAS 7709-58-2], and 2-(R)-methyl-1-(2-(S)-pyrrolidinylmethyl)pyrrolidine. MS (ES+) m/e 404.2

EXAMPLE 8

[2,6-Difluoro-4-(thiazol-4-ylmethoxy)-phenyl]-[2-(S)-(2-(R)-methyl-pyrrolidin-1-ylmethyl)-pyrrolidin-1-yl]-methanone

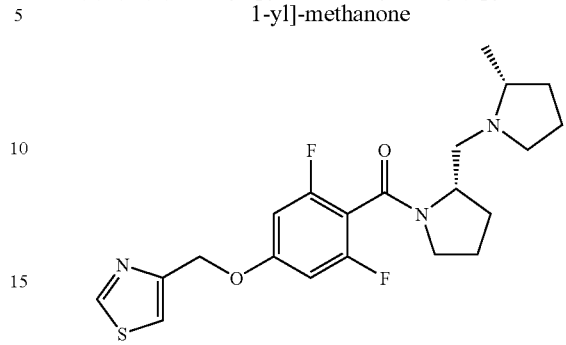

The title compound is prepared in a manner substantially analogous to Procedures D and E using 2,6-difluoro-4-hydroxy-benzoic acid methyl ester [CAS 194938-88-0], 4-(chloromethyl)thiazole hydrochloride [CAS 7709-58-2], and 2-(R)-methyl-1-(2-(S)-pyrrolidinylmethyl)pyrrolidine. MS (ES+) m/e 422.2

EXAMPLE 9

[2-Fluoro-4-(2methyl-thiazol-4-ylmethoxy)-phenyl]-(2-(S)-pyrrolidin-1-ylmethyl-pyrrolidin-1-yl)-methanone

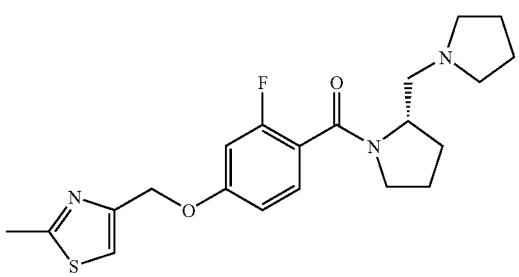

The title compound is prepared in a manner substantially analogous to Procedures D and E using 2-fluoro-4-hydroxy-benzoic acid methyl ester [CAS 197507-22-5], 4-chloromethyl-2-methylthiazole hydrochloride [CAS 39238-07-8], and (S)(+)-1-(2-pyrrolidinylmethyl)pyrrolidine. MS (ES+) m/e 404.2

EXAMPLE 10

[2-Fluoro-4-(thiophen-3-ylmethoxy)-phenyl]-(2-(S)-pyrrolidin-1-ylmethyl-pyrrolidin-1-yl)-methanone

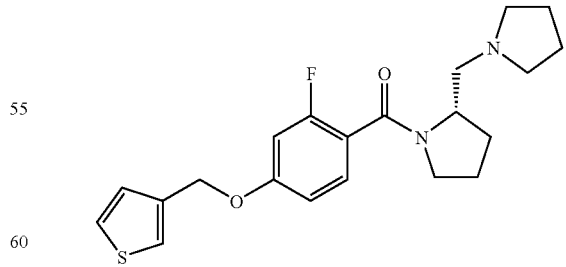

The title compound is prepared in a manner substantially analogous to Procedures D and E using 2-fluoro-4-hydroxy-benzoic acid methyl ester [CAS 197507-22-5], 3-chloromethyl-thiophene [CAS 2746-23-8], and (S)(+)-1-(2-pyrrolidinylmethyl)pyrrolidine. MS (ES+) m/e 389.2

EXAMPLE 11

[2-Fluoro-4-(thiophen-3-ylmethoxy)-phenyl]-[2-(S)-(2-(R)-methyl-pyrrolidin-1-ylmethyl)-pyrrolidin-1-yl]-methanone

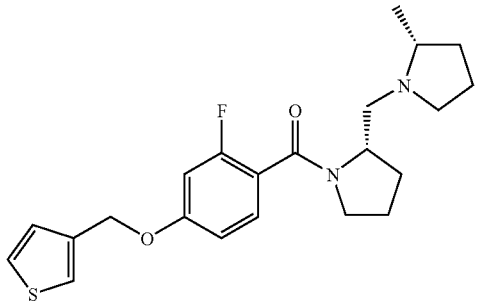

The title compound is prepared in a manner substantially analogous to Procedures D and E using 2-fluoro-4-hydroxy-benzoic acid methyl ester [CAS 197507-22-5], 3-chloromethyl-thiophene [CAS 2746-23-8], and 2-(R)-Methyl-1-(2-(S)-pyrrolidinylmethyl)pyrrolidine. MS (ES+) m/e 403.3

EXAMPLE 12

[2-Fluoro-4-(thiophen-2-ylmethoxy)-phenyl]-(2-(S)-pyrrolidin-1-ylmethyl-pyrrolidin-1-yl)-methanone

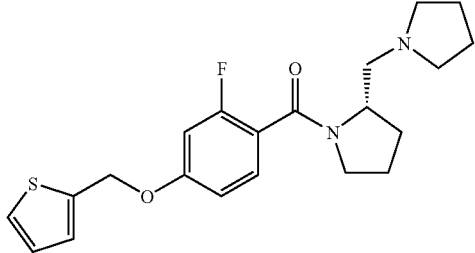

The title compound is prepared in a manner substantially analogous to Procedures D and E using 2-fluoro-4-hydroxy-benzoic acid methyl ester [CAS 197507-22-5], 2-chloromethyl-thiophene [CAS 765-50-4], and (S)(+)-1-(2-pyrrolidinylmethyl)pyrrolidine. MS (ES+) m/e 389.2

EXAMPLE 13

[2-Fluoro-4-(thiophen-2-ylmethoxy)-phenyl]-[2-(S)-(2-(R)-methyl-pyrrolidin-1-ylmethyl)-pyrrolidin-1-yl]-methanone

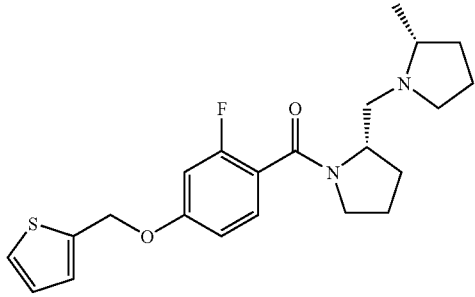

The title compound is prepared in a manner substantially analogous to Procedures D and E using 2-fluoro-4-hydroxy-benzoic acid methyl ester [CAS 197507-22-5], 2-chloromethyl-thiophene [CAS 2746-23-8], and 2-(R)-methyl-1-(2-(S)-pyrrolidinylmethyl)pyrrolidine. MS (ES+) m/e 403.3

EXAMPLE 14

5-{3-Fluoro-4-[2-(S)-(2-(R)-methyl-pyrrolidin-1-ylmethyl)-pyrrolidine-1-carbonyl]-phenoxymethyl}-thiophene-2-carbonitrile

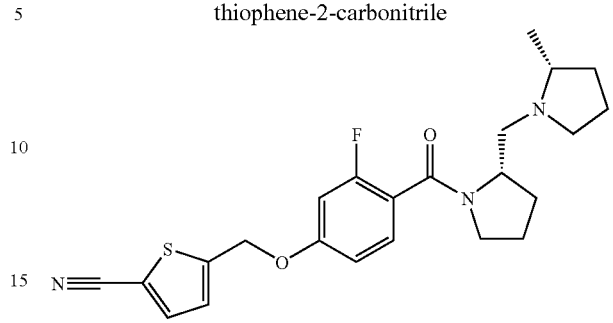

The title compound is prepared in a manner substantially analogous to Procedures D and E using 2-fluoro-4-hydroxy-benzoic acid methyl ester [CAS 197507-22-5], 5-bromomethyl-thiophene-2-carbonitrile [CAS 134135-41-4], and 2-(R)-methyl-1-(2-(S)-pyrrolidinylmethyl)pyrrolidine. MS (ES+) m/e 428.3

EXAMPLE 15

[2-Fluoro-4-(2-methyl-thiazol-4-ylmethoxy)-phenyl]-[2-(S)-(2-(R)-methyl-pyrrolidin-1-ylmethyl)-pyrrolidin-1-yl]-methanone

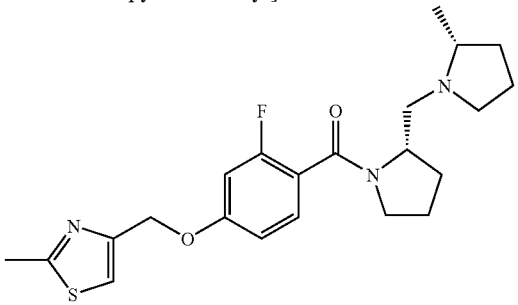

The title compound is prepared in a manner substantially analogous to Procedures D and E using 2-fluoro-4-hydroxy-benzoic acid methyl ester [CAS 197507-22-5], 4-chloromethyl-2-methylthiazole hydrochloride [CAS 39238-07-8], and 2-(R)-methyl-1-(2-(S)-pyrrolidinylmethyl)pyrrolidine. MS (ES+) m/e 418.2

EXAMPLE 16

4-{3-Fluoro-4-[2-(S)-(2-(R)-methyl-pyrrolidin-1-ylmethyl)-pyrrolidine-1-carbonyl]-phenoxymethyl}-thiophene-2-carbonitrile

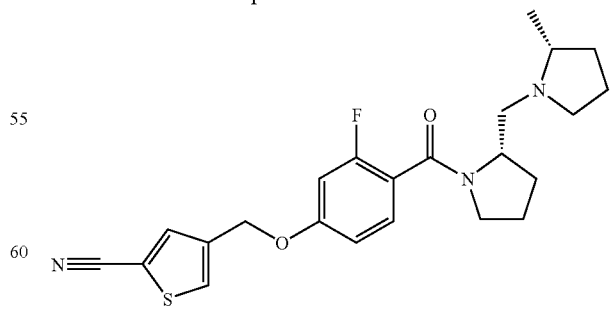

The title compound is prepared in a manner substantially analogous to Procedure C from (2-Fluoro-4-hydroxy-phenyl)-[2-(S)-(2-(R)-methyl-pyrrolidin-1-ylmethyl)-pyrrolidin-1-yl]-methanone and 4-bromomethyl-thiophene-2-carbonitrile [CAS 186552-07-8]. MS (ES+) m/e 428.3

EXAMPLE 17

[2-Fluoro-4-([1,2,4]oxadiazol-3-ylmethoxy)-phenyl]-[2-(S)-(2-(R)-methyl-pyrrolidin-1-ylmethyl)-pyrrolidin-1-yl]-methanone trifluoroacetate salt

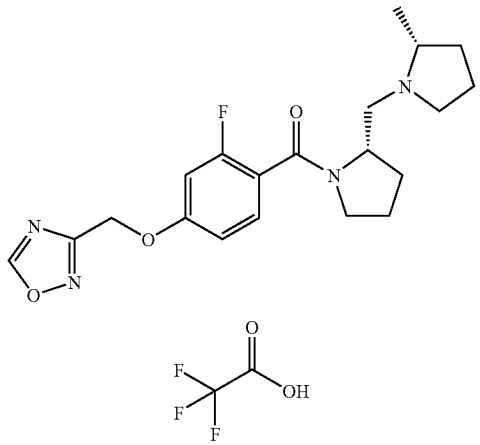

The title compound is prepared in a manner substantially analogous to Procedure D from (2-Fluoro-4-hydroxy-phenyl)-[2-(S)-(2-(R)-methyl-pyrrolidin-1-ylmethyl)-pyrrolidin-1-yl]-methanone and 3-(chloromethyl)-1,2,4-oxadiazole [CAS 51791-12-9]. The crude product is purified by reversed phase chromatography to provide the desired product as a trifluoroacetate salt. MS (ES+) m/e 389.2

EXAMPLE 18

[2-Fluoro-4-(5-methyl-isoxazol-3-ylmethoxy)-phenyl]-[2-(S)-(2-(R)-methyl-pyrrolidin-1-ylmethyl)-pyrrolidin-1-yl]-methanone trifluoroacetate salt

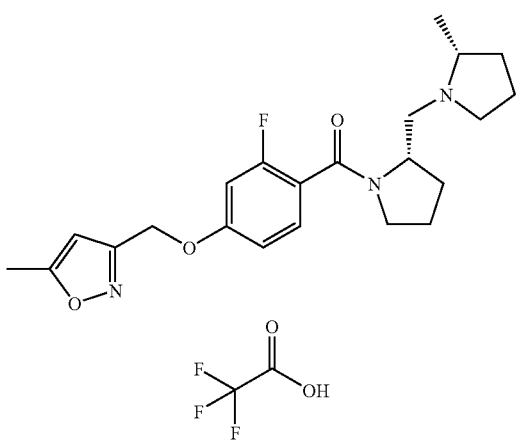

The title compound is prepared in a manner substantially analogous to Procedure D from (2-Fluoro-4-hydroxy-phenyl)-[2-(S)-(2-(R)-methyl-pyrrolidin-1-ylmethyl)-pyrrolidin-1-yl]-methanone and 3-(chloromethyl)-5-methylisoxazole [CAS 35166-37-1]. The crude product is purified by reversed phase chromatography to provide the desired product as a trifluoroacetate salt. MS (ES+) m/e 402.2

EXAMPLE 19

[2-Fluoro-4-(5-trifluoromethyl-furan-2-ylmethoxy)-phenyl]-[2-(S)(2-(R)-methyl-pyrrolidin-1-ylmethyl)-pyrrolidin-1-yl]-methanone trifluoroacetate salt

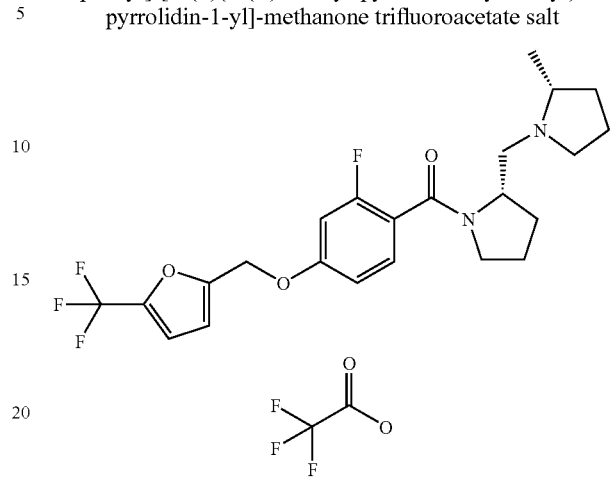

The title compound is prepared in a manner substantially analogous to Procedure C from (2-Fluoro-4-hydroxy-phenyl)-[2-(S)-(2-(R)-methyl-pyrrolidin-1-ylmethyl)-pyrrolidin-1-yl]-methanone and 2-(bromomethyl)-5-(trifluoromethyl)furan [CAS 17515-77-4]. The crude product is purified by reversed phase chromatography to provide the desired product as a trifluoroacetate salt. MS (ES+) m/e 455.3

EXAMPLE 20

5-{3-Fluoro-4-[2-(S)-(2-(R)-methyl-pyrrolidin-1-ylmethyl)-pyrrolidine-1-carbonyl]-phenoxymethyl}-thiophene-3-carbonitrile

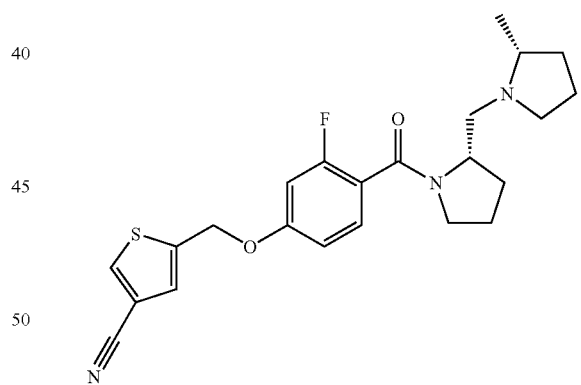

The title compound is prepared in a manner substantially analogous to Procedure C from (2-Fluoro-4-hydroxy-phenyl)-[2-(S)-(2-(R)-methyl-pyrrolidin-1-ylmethyl)-pyrrolidin-1-yl]-methanone and 5-(bromomethyl) 3-thiophenecarbonitrile [CAS 186552-10-3]. MS (ES+) m/e 428.3

The pharmaceutical salts of the invention are typically formed by reacting a compound of Formula I or Formula II with an equimolar or excess amount of acid or base. The reactants are generally combined in a mutual solvent such as diethylether, tetrahydrofuran, methanol, ethanol, isopropanol, benzene, and the like, for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, for example argon or nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or Formula II may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or Formula II is preferably formulated in a unit dosage form prior to administration. Therefore, yet another embodiment of the present invention is a pharmaceutical composition comprising a compound of Formula I or Formula II and one or more pharmaceutically acceptable carriers, diluents, or excipients. The present pharmaceutical compositions are prepared by known procedures using well-known and readily available ingredients. Preferably the compound is administered orally. Preferably, the pharmaceutical composition is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Compounds of Formula I or Formula II are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I or Formula II are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels, and possibly the level of other monoamines, resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types, and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (Preparation of Histamine Receptor Subtype Membranes) for the histamine receptor subtypes.

Membranes isolated as described in (Preparation of Histamine Receptor Subtype Membranes) were used in a [35S] GTPχS functional assay. Binding of [35S]GTPχS to membranes indicates agonist activity. Compounds of the invention of Formula I or Formula II were tested for their ability to inhibit binding in the presence of agonists. Alternately, the same transfected cell lines were used for a cAMP assay wherein H3R agonists inhibited forskolin-activated synthesis of cAMP. Compounds of Formula I or Formula II were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitogen) and transfected into HEK293 cells using the FuGENE Tranfection Reagent (Roche Diagnostics Corporation). Transfected cells were selected using G418 (500 μ/mL). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 nM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 μl). Astemizole (10 μM, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 mL assay buffer, mixed by vortexing, and centrifuged (40,000 g at 4° C.) for 10 minutes. The pellet resuspension, vortexing, and centrifugation was repeated 2 more times. The final cell pellet was resuspended in 30 mL and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 μl). Cimetidine (10 μM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 μ/mL), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM ($^3$H)-n-alpha-methylhistamine (NEN, NET1027) (total volume per well=200 μl). Thioperimide was added to determine non-specific binding. Several clones were selected as positive for binding, and a single clone (H3R8) was used to prepare membranes for binding studies described herein. Five micrograms of protein was used per well in the SPA receptor-binding assay.

D. Preparation of GPRv53 Membranes cDNA for the human GPRv53 receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/mL G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harvester. Filters were counted with melt-on scintillator sheets (Perkin Elmer) in a Wallac Trilux 1450 Microbeta Scintillation counter for 5 minutes.

Pharmacological Results cAMP ELISA

HEK293 H3R8 cells prepared as described above were seeded at a density of 50,000 cells/well and grown overnight in DMEM/F12 (Gibco) supplemented with 5% FBS and 500 ug/mL G418. The next day tissue culture medium was removed and replaced with 50 μl cell culture medium containing 4 mM 3-isobutyl-1-methylxanthine (Sigma) and incubated for 20 minutes at room temperature. Antagonist were added in 50 μl cell culture medium and incubated for 20 minutes at room temperature. Agonist R (−)α methylhistamine (RBI) at a dose response from $1 \times 10^{-10}$ to $1 \times 10^{-5}$ M was then added to the wells in 50 μl cell culture medium and incubated for 5 minutes at room temperature. Then 50 μl of cell culture medium containing 20 μM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTP γ[S] Binding Assay

Antagonist activity of selected compounds was tested for inhibition of [35S] GTP γ[S] binding to H3R membranes in the presence of agonists. Assays were run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 μl assay buffer. Antagonist was then added to the wells in a volume of 50 μl assay buffer and incubated for 15 minutes at room temperature. Agonist R(−) alpha methylhistamine (RBI) at either a dose response from $1 \times 10^{-10}$ to $1 \times 10^{-5}$ M or fixed concentration of 100 nM were then added to the wells in a volume of 50 μl assay buffer and incubated for 5 minutes at room temperature. GTPγ[35S] was added to each well in a volume of 50 μl assay buffer at a final concentration of 200 pM, followed by the addition of 50 μl of 20 mg/mL WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a Ki (nM).

All compounds set forth in the examples exhibit affinity for the H3 receptor greater than 1 uM in the H3R binding assay. Preferred compounds of the invention exhibit affinity for the H3 receptor greater than 200 nM. Most preferred compounds of the invention exhibit affinity for the H3 receptor greater than 20 nM. The results are given below for the indicated compound.

TABLE 2

| Example | Human H3 Receptor Ki (nM) |
|---|---|
| 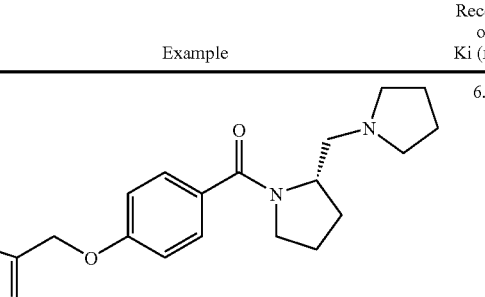 | 6.2 |
| 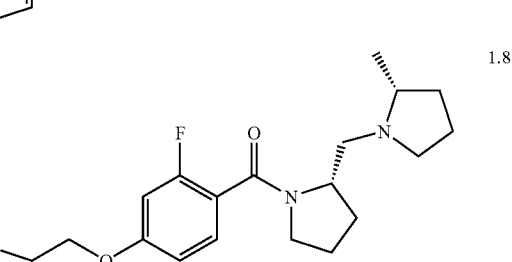 | 1.8 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

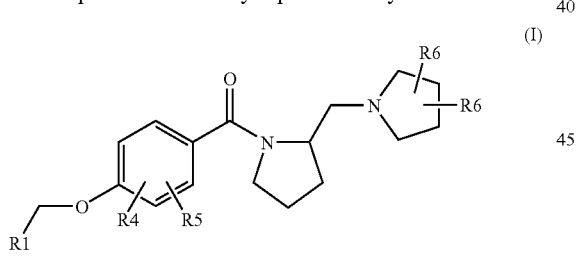

(I)

wherein;

R1 is independently

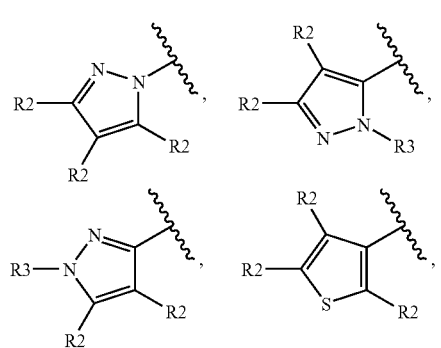

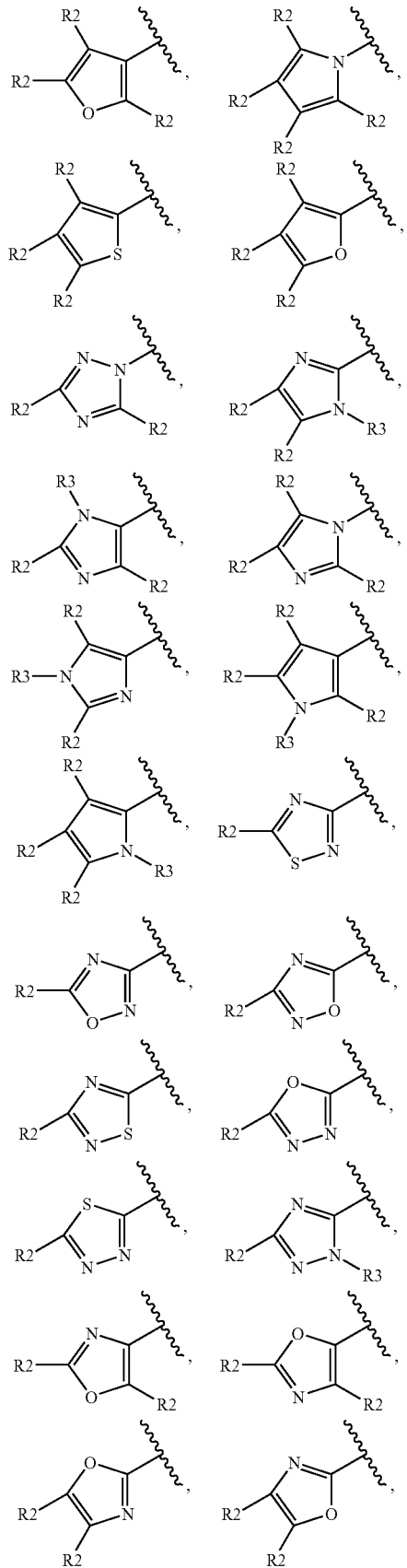

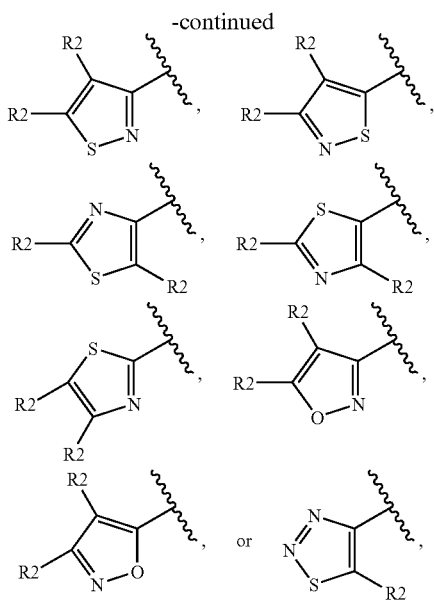

wherein the bond directed to the zig-zag lines indicates the point of attachment to the position indicated by R1 in Formula I;

R2 is independently at each occurrence
— H, -halogen, —($C_1$-$C_3$) alkyl (optionally substituted with one to three halogens), —CN, —C(O)R7, —C(O)OR7, —CO(O)Li, —C(O)($C_3$-$C_5$)cycloalkyl, C(O)NR7R8, —$OCF_3$, —OR7, —$NO_2$, —NR7R8, —$NR9SO_2$R7, —NR9C(O)R7, —$NR9CO_2$R7, —NR9C(O)NR7R8, —SR7, —$SO_2$R7, —$SO_2CF_3$, —$SO_2$NR7R8, or —S(O)R7;

R3 is independently at each occurrence
— H, —($C_1$-$C_3$) alkyl (optionally substituted with one to three halogens), —$SO_2$R7, —C(O)R7, —C(O)NR7R8, or —C(O)OR7;

R4 and R5 are independently
— H, —OH, -halogen, —($C_1$-$C_3$) alkyl (optionally substituted with one to three halogens), or —OR9;

R6 is independently at each occurrence
— H, -halogen, —($C_1$-$C_3$) alkyl (optionally substituted with one to three halogens), —$NH_2$, —NR7R8, —OH, or —OR7;

R7 and R8 are independently at each occurrence
— H, or —($C_1$-$C_2$) alkyl (optionally substituted with one to three halogens), wherein R7 and R8 can combine with the atom to which they are attached to form a four to six membered ring; and R9 is independently at each occurrence
— H or —($C_1$-$C_3$) alkyl (optionally substituted with one to three halogens); or a stereoisomer thereof; or a pharmaceutically acceptable salt thereof.

2. The compound of claim 1, wherein
R1 is independently

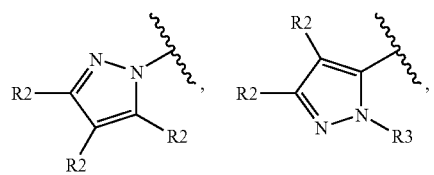

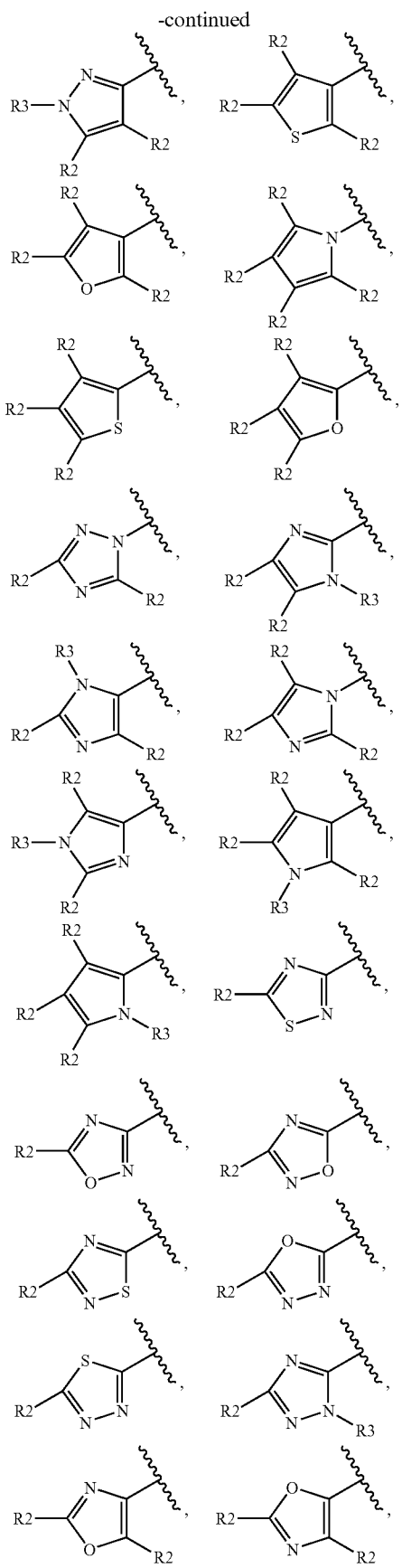

-continued

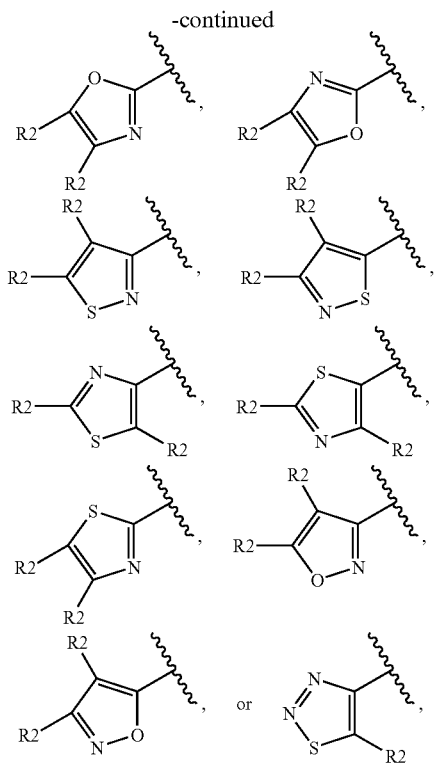

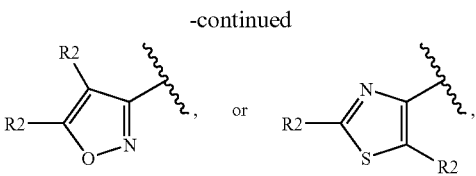

wherein the bond directed to the zig-zag lines indicates the point of attachment to the position indicated by R1 in Formula I;

R2 is independently at each occurrence
—H, -halogen, —($C_1$-$C_3$) alkyl (optionally substituted with one to three halogens), or —CN;

R4 and R5 are independently —H or -halogen; and

One occurrence of R6 is —H, and the second occurrence of R6 is independently —H, -halogen, or —($C_1$-$C_3$) alkyl (optionally substituted with one to three halogens); or a stereoisomer thereof; or a pharmaceutically acceptable salt thereof.

4. The compound of claim 1, wherein,

R1 is independently

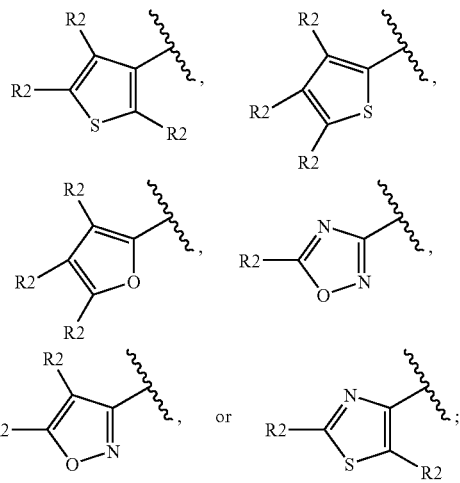

R2 is —H, —$CH_3$, —$CF_3$, or —CN; R4 is -hydrogen or —R5 is -hydrogen or —F; One occurrence of R6 is —H, and the second occurrence of R6 is —H or —$CH_3$; or a stereoisomer thereof; or a pharmaceutically acceptable salt thereof.

5. The compound of claim 1 wherein R4 and R5 are —H; or a stereoisomer thereof; or a pharmaceutically acceptable salt thereof.

6. The compound of claim 1 wherein R4 is halogen and R5 is —H; or a stereoisomer thereof; or a pharmaceutically acceptable salt thereof.

7. The compound of claim 1 wherein one occurrence of R6 is —H, and the second occurrence of R6 is —$CH_3$; or a stereoisomer thereof; or a pharmaceutically acceptable salt thereof.

8. The compound of claim 1, selected from the group consisting of formulae X1 to X20:

wherein the bond directed to the zig-zag lines indicates the point of attachment to the position indicated by R1 in Formula I;

R2 is independently at each occurrence
—H, -halogen, —($C_1$-$C_3$) alkyl (optionally substituted with one to three halogens), or —CN;

R3 is independently at each occurrence
—H or —($C_1$-$C_3$) alkyl (optionally substituted with one to three halogens);

R4 and R5 are independently —H or -halogen; and

One occurrence of R6 is —H, and the second occurrence of R6 is independently —H, -halogen, or —($C_1$-$C_3$) alkyl (optionally substituted with one to three halogens); or a stereoisomer thereof; or a pharmaceutically acceptable salt thereof.

3. The compound of claim 2, wherein,

R1 is independently

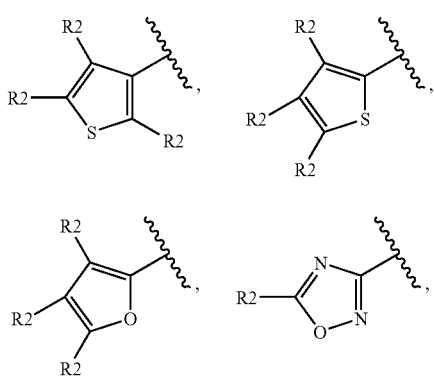

| Formula Number | Structure |
| --- | --- |
| X1 | 5-({[4-({2-[(pyrrolidin-1-yl)methyl]pyrrolidin-1-yl}carbonyl)phenoxy]methyl})thiophene-2-carbonitrile |
| X2 | {4-[(1,3-thiazol-4-yl)methoxy]phenyl}{2-[(pyrrolidin-1-yl)methyl]pyrrolidin-1-yl}methanone |
| X3 | {2-fluoro-4-[(1,3-thiazol-4-yl)methoxy]phenyl}{2-[(pyrrolidin-1-yl)methyl]pyrrolidin-1-yl}methanone |
| X4 | {4-[(furan-2-yl)methoxy]phenyl}{2-[(pyrrolidin-1-yl)methyl]pyrrolidin-1-yl}methanone |
| X5 | 5-({[3-fluoro-4-({2-[(pyrrolidin-1-yl)methyl]pyrrolidin-1-yl}carbonyl)phenoxy]methyl})thiophene-2-carbonitrile |
| X6 | {2,6-difluoro-4-[(1,3-thiazol-4-yl)methoxy]phenyl}{2-[(pyrrolidin-1-yl)methyl]pyrrolidin-1-yl}methanone |

-continued

| Formula Number | Structure |
|---|---|
| X7 | 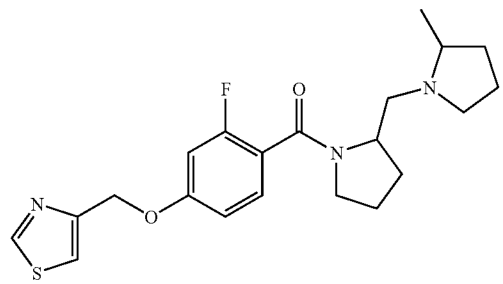 |
| X8 | 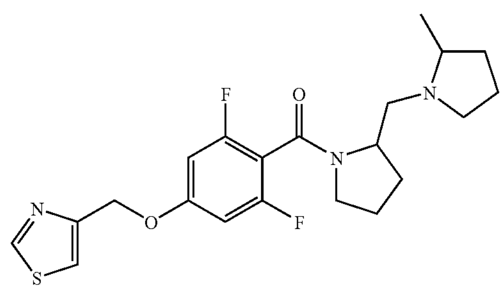 |
| X9 | 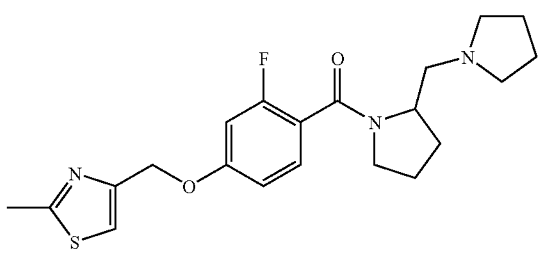 |
| X10 | 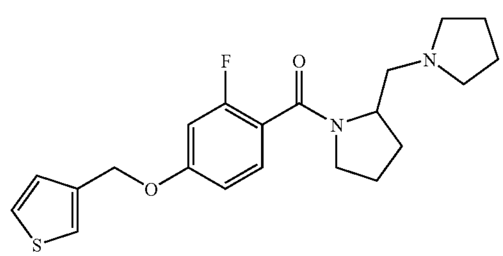 |
| X11 | 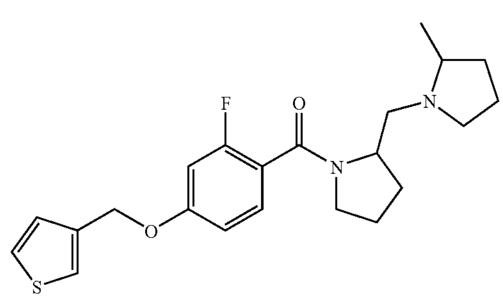 |

-continued
| Formula Number | Structure |
|---|---|
| X12 | 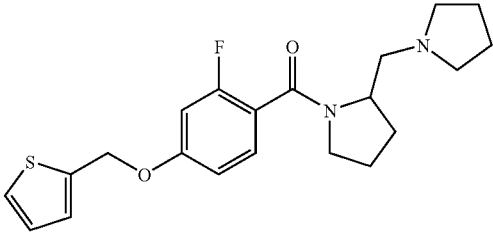 |
| X13 | 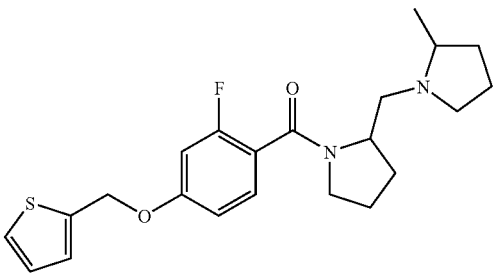 |
| X14 | 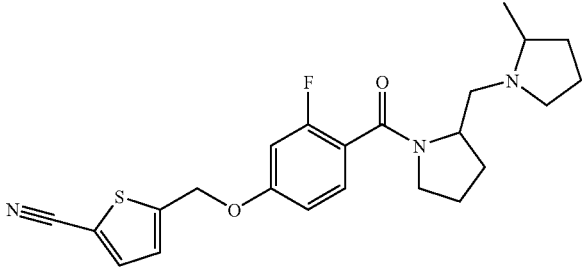 |
| X15 | 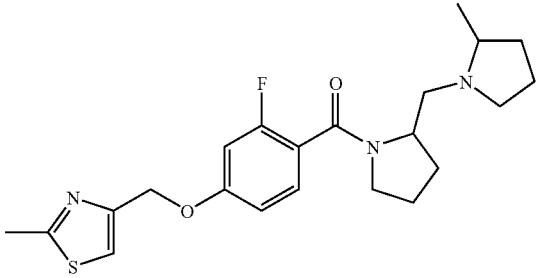 |
| X16 | 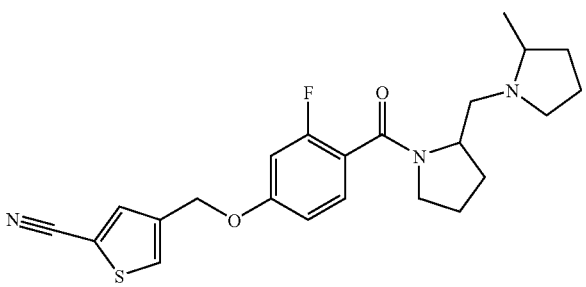 |

-continued

| Formula Number | Structure |
|---|---|
| X17 | 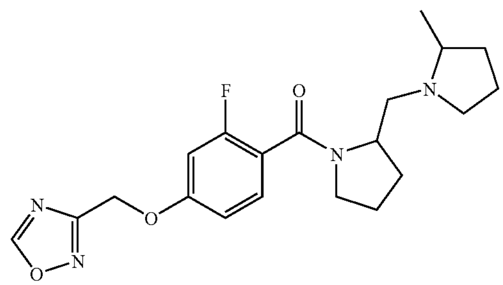 |
| X18 | 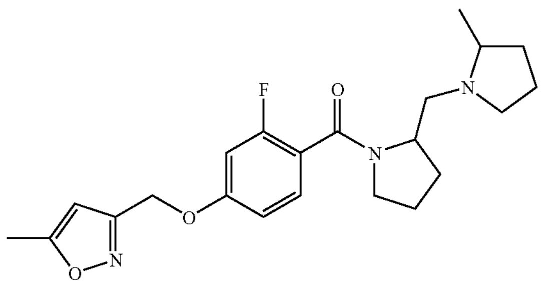 |
| X19 | 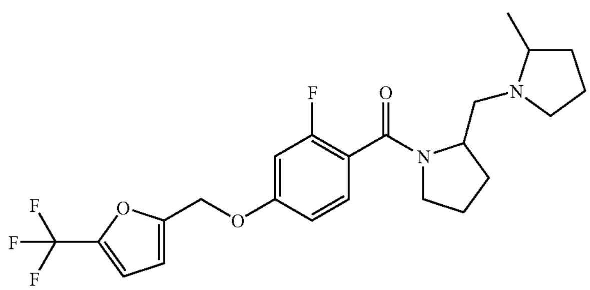 |
| X20 | | or a pharmaceutically acceptable salt thereof.

9. A compound of claim 1 selected from the group consisting of
5-[4-(2-(S)-Pyrrolidin-1-ylmethyl-pyrrolidine-1-carbonyl)-phenoxymethyl]-thiophene-2-carbonitrile;
(2-(S)-Pyrrolidin-1-ylmethyl-pyrrolidin-1-yl)-[4-(thiazol-4-ylmethoxy)-phenyl]-methanone;
[2-Fluoro-4-(thiazol-4-ylmethoxy)-phenyl]-(2-(S)-pyrrolidin-1-ylmethyl-pyrrolidin-1-yl)-methanone;
[4-(Furan-2-ylmethoxy)-phenyl]-(2-(S)-pyrrolidin-1-ylmethyl-pyrrolidin-1-yl)-methanone;
5-[3-Fluoro-4-(2-(S)-pyrrolidin-1-ylmethyl-pyrrolidine-1-carbonyl)-phenoxymethyl]-thiophene-2-carbonitrile;
[2,6-Difluoro-4-(thiazol-4-ylmethoxy)-phenyl]-(2-(S)-pyrrolidin-1-ylmethyl-pyrrolidin-1-yl)-methanone;
[2-Fluoro-4-(thiazol-4-ylmethoxy)-phenyl]-[2(S)-(2-(R) methyl-pyrrolidin-1-ylmethyl)-pyrrolidin-1-yl]-methanone;
[2,6-Difluoro-4-(thiazol-4-ylmethoxy)-phenyl]-[2-(S)-(2-(R)-methyl-pyrrolidin-1-ylmethyl)-pyrrolidin-1-yl]-methanone;
[2-Fluoro-4-(2-methyl-thiazol-4-ylmethoxy)-phenyl]-(2-(S)-pyrrolidin-1-ylmethyl-pyrrolidin-1-yl)-methanone;
[2-Fluoro-4-(thiophen-3-ylmethoxy)-phenyl]-(2-(S)-pyrrolidin-1-ylmethyl-pyrrolidin-1-yl)-methanone;

[2-Fluoro-4-(thiophen-3-ylmethoxy)-phenyl]-[2-(S)-(2-(R)-methyl-pyrrolidin-1-ylmethyl)-pyrrolidin-1-yl]-methanone;

[2-Fluoro-4-(thiophen-2-ylmethoxy)-phenyl]-(2-(S)-pyrrolidin-1-ylmethyl-pyrrolidin-1-yl)-methanone;

[2-Fluoro-4-(thiophen-2-ylmethoxy)-phenyl]-[2-(S)-(2-(R)-methyl-pyrrolidin-1-ylmethyl)-pyrrolidin-1-yl]-methanone;

5-{3-Fluoro-4-[2-(S)-(2-(R)-methyl-pyrrolidin-1-ylmethyl)-pyrrolidine-1-carbonyl]-phenoxymethyl}-thiophene-2-carbonitrile;

[2-Fluoro-4-(2-methyl-thiazol-4-ylmethoxy)-phenyl]-[2-(S)-(2-(R)-methyl-pyrrolidin-1-ylmethyl)-pyrrolidin-1-yl]-methanone;

4-{3-Fluoro-4-[2-(S)-(2-(R)-methyl-pyrrolidin-1-ylmethyl)-pyrrolidine-1-carbonyl]-phenoxymethyl}-thiophene-2-carbonitrile;

[2-Fluoro-4-([1,2,4]oxadiazol-3-ylmethoxy)-phenyl]-[2-(S)-(2-(R)-methyl-pyrrolidin-1-ylmethyl)-pyrrolidin-1-yl]-methanone;

[2-Fluoro-4-(5-methyl-isoxazol-3-ylmethoxy)-phenyl]-[2-(S)-(2-(R)-methyl-pyrrolidin-1-ylmethyl)-pyrrolidin-1-yl]-methanone;

[2-Fluoro-4-(5-trifluoromethyl-furan-2-ylmethoxy)-phenyl]-[2-(S)(2-(R)-methyl-pyrrolidin-1-ylmethyl)-pyrrolidin-1-yl]-methanone; and 5-{3-Fluoro-4-[2-(S)-(2-(R)-methyl-pyrrolidin-1-ylmethyl)-pyrrolidine-1-carbonyl]-phenoxymethyl}-thiophene-3-carbonitrile;

or a pharmaceutically acceptable salt thereof.

10. A pharmaceutical composition which comprises a compound or salt of claim 1 and a pharmaceutically acceptable carrier.

11. A method for treatment of obesity which comprises administering to a mammal in need of such treatment an effective amount of a compound or salt of claim 1.

12. A method for treatment of obesity which comprises administering to a mammal in need of such treatment an effective amount of a pharmaceutical composition of claim 10.

* * * * *